(12) United States Patent
Schweitzer et al.

(10) Patent No.: US 7,186,813 B1
(45) Date of Patent: Mar. 6, 2007

(54) BIOMOLECULES HAVING MULTIPLE ATTACHMENT MOIETIES FOR BINDING TO A SUBSTRATE SURFACE

(75) Inventors: Markus Schweitzer, Frankfurt am Main (DE); Norbert Windhab, Hofheim am Taunus (DE); John R. Havens, Arlington, MA (US); Thomas J. Onofrey, Poway, CA (US); Charles Greef, Boulder, CO (US); Daguang Wang, Carlsbad, CA (US)

(73) Assignee: Nanogen Recognomics GmbH, Frankfurt (DE)

( * ) Notice: Subject to any disclaimer, the term of this patent is extended or adjusted under 35 U.S.C. 154(b) by 535 days.

(21) Appl. No.: 10/181,207

(22) PCT Filed: Aug. 11, 2000

(86) PCT No.: PCT/US00/22205

§ 371 (c)(1),
(2), (4) Date: Jul. 10, 2002

(87) PCT Pub. No.: WO01/51689

PCT Pub. Date: Jul. 19, 2001

(51) Int. Cl.
C07H 21/00 (2006.01)
C07H 21/02 (2006.01)
C07H 21/04 (2006.01)
C12Q 1/68 (2006.01)

(52) U.S. Cl. .................. 536/23.1; 536/25.3; 536/25.33; 435/6

(58) Field of Classification Search ............... 536/23.1, 536/25.3, 25.33; 435/6
See application file for complete search history.

(56) References Cited

U.S. PATENT DOCUMENTS

| 5,476,665 | A | 12/1995 | Dennison | 424/484 |
| 5,543,054 | A | 8/1996 | Charkoudian et al. | 210/638 |
| 5,605,662 | A | 2/1997 | Heller et al. | 422/68.1 |
| 5,807,522 | A | 9/1998 | Brown et al. | 422/50 |
| 5,830,655 | A | 11/1998 | Monforte et al. | |
| 5,837,859 | A | 11/1998 | Teoule et al. | 536/25.3 |
| 5,869,466 | A | 2/1999 | Russell-Jones et al. | |
| 5,929,208 | A | 7/1999 | Heller et al. | 530/333 |
| 5,986,076 | A | 11/1999 | Rothschild et al. | 536/22.1 |
| 6,011,020 | A | 1/2000 | Gold et al. | 514/44 |

FOREIGN PATENT DOCUMENTS

| EP | 0 361 768 A2 | 4/1990 |
| EP | 0816368 | 1/1998 |
| WO | WO 85/05638 A | 12/1985 |
| WO | WO 90/03401 A | 4/1990 |
| WO | WO 00/29373 | 5/2000 |
| WO | WO 01/07657 A1 | 2/2001 |
| WO | WO 01/09385 | 2/2001 |
| WO | WO 01/51689 | 7/2001 |

OTHER PUBLICATIONS

Boullanger et al. J. Carbohydrate Chemistry 4(3), 279-291, 1985.*
Beier, M., et al. "Versatile derivatisation of solid support media for covalent bonding on DNA-microchips." Nucleic Acids Research 27(9): 1970-77 (1999).
Raddatz, S., et al. "Hydrazide oligonucleotides: new chemical modification for chip array attachment and conjugation." Nucleic Acids Research 30(21): 4793-4802 (2002).
Timofeev et al., "Regioselective immobilization of short oligonucleotides to acrylic copolymer gels," Nucleic Acids Research 24(16):3142-3148.
Anderson & Kaplan. "Enzymatic Studies with Analogues of Diphosphopyridine Nucleotide." Journal of Biological Chemistry 234(5): 1226-32 (1959).
Fehlhaber, H-W., et al. "Moenomycin A: A Structural Revision and New Structure-Activity Relations" Tetrahedron 46(5): 1557-68 (1990).
Ghosh, S., et al. "Synthesis of 5' Oligonucleotide Hydrazide Derivatives and Their Use in Preparation of Enzyme-Nucleic Acid Hybridization Probes." Analytical Biochemistry 178(1): 43-51 (1989).
Guzaev, A., et al. "Solid Support Synthesis of Ester Linked Hydrophobic Conjugates of Oligonucleotides." Tetrahedron 55(30): 9101-9116 (Jul. 23, 1999).
Vogel, K.W., et al. "A Reversed Thioester Analogue of Acetyl-Coenzyme A: An Inhibitor of Thiolase and a Synthon for Other Acyl-CoA Analogues" J. Amer. Chem. Soc. 120(14): 3275-83 (Apr. 15, 1998).

* cited by examiner

Primary Examiner—Jezia Riley
(74) Attorney, Agent, or Firm—O'Melveny & Myers LLP

(57) ABSTRACT

Biomolecules are provided having multiple binding sites for attachment to a substrate surface. The multiple attachment sites may be produced directly on the biomolecule or through use of branched phosphoramidite moieties that can be added in multiple to form dendritic structures which can in turn provide attachment sites for substrate binding moieties. Substrate binding moieties may include noncovalent binding moieties. For covalent binding moieties oligonucleotides containing hydrazides are provided. These hydrazides can be introduced via protected building blocks such as phosphoramidites or via building blocks containing precursor forms of such hydrazides.

11 Claims, 35 Drawing Sheets

Scheme 1

Scheme 2

Scheme 3

US 7,186,813 B1

BIOMOLECULES HAVING MULTIPLE ATTACHMENT MOIETIES FOR BINDING TO A SUBSTRATE SURFACE

FIELD OF THE INVENTION

This invention relates to attachment chemistries for binding biomolecules to a substrate surface. More particularly, this invention relates to attachment chemistries involving branched structures for providing biomolecules having multiplicities of chemical binding moieties for binding the biomolecules to a substrate surface.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

The immobilization of oligonucleotides on substrates is an important and necessary step for many applications such as DNA chip technology, surface plasmon resonance experiments, or other biosensor applications. Classically, oligonucleotides are immobilized onto substrates by modification of the 3'- or 5'-end with one reactive group e.g. an amine, thiol or aldehyde (covalent attachment) or group forming stable complexes e.g. biotin, phenylboronic acid etc. (non-covalent attachment). The modified oligonucleotides are then addressed to the location where the immobilization is desired and reacted with an appropriate functional group such as an aldehyde, maleimide, hydrazide etc. or complexed with a binding molecule such as streptavidin, etc. The addressing to specific locations on a substrate can be done by spotting (pin or drop deposition), by electronic addressing, or by a variety of other processes. In some cases the reaction for the immobilization is slow and requires long (overnight) incubation of the oligonucleotides on the substrate. These immobilization reactions may also be reversible, resulting in the release of the biomolecule over time.

In other instances, dendrimeric structures on biomolecules has been described (e.g., WO 99/10362, WO 96/19240, and WO 99/43287), but the use of the dendrimeric structures have been directed toward providing signal sites such as for detection while the biomolecule itself is simply attached to a substrate using classical means.

In contrast thereto, the present invention describes an improved process for immobilization of biomolecules using oligonucleotides containing multiple reactive sites, i.e. nucleophiles, electrophiles, and Lewis acids or bases. The advantage of this approach is a higher rate of immobilization, a higher stability of the attachment, and the potential to obtain higher amounts of immobilized oligonucleotide onto the substrate surface. These gains are independent of the approach used for the immobilization. Oligonucleotides with multiple attachment sites can be obtained with both covalent and noncovalent attachment chemistries.

Furthermore the present invention describes the preparation of oligonucleotides containing one or more hydrazides. Hydrazides are nucleophilic reactive groups that can be used for any type of conjugation reaction. They can react, for example, with electrophilic aldehydes forming hydrazones (which can be further stabilized by reduction) and with active esters forming stable covalent linkages, see FIG. 18. This chemistry can be used for attaching fluorophores, proteins or peptides, reporter groups and other oligomers to oligonucleotides. The reactions of hydrazides can also be used for the immobilization of biomolecules onto substrates. Such hydrazide modified oligonucleotides have not been previously described.

The advantages of this invention within the scope of this description are numerous. For example, this invention uses a short reaction time, allows for multiple binding sites per bound entity, provides for stability to a relatively broad pH range, and provides for the capability of attachment under both anhydrous or aqueous conditions thereby providing an improved method for attaching molecules to any solid phase surface for any applicable use. The invention is useful for solid phase synthesis and/or synthesis of small molecule libraries such as biomolecules including, but not limited to, DNA, RNA, PNA, p-RNA (pyranosyl-RNA), and peptides. The invention is also useful for analytical techniques that require an immobilized reagent such as, without limitation, hybridization based assays, diagnostics, gene sequence identification and the like.

SUMMARY OF THE INVENTION

In a first embodiment of the invention, biomolecules are provided having a multiplicity of branched or dendrimeric moieties for connecting thereto functional or reactive moieties for binding to a substrate surface.

The use of oligonucleotides with multiple reactive sites or complexing agents within one oligonucleotide offers significant advantages to this immobilization process. First, it increases the speed of the immobilization process. One reason for this effect is that chance for an initial contact between the attachment partners by diffusion is higher when one oligonucleotide bears multiple reactive sites. Additionally, the oligonucleotide can be immobilized via secondary and multiple covalent or noncovalent linkages which are formed after (or simultaneous with) the primary linkage. The formation of these secondary linkages is then an intramolecular process that is kinetically favored to the intermolecular primary linkage formation. This is another reason for the higher immobilization rate.

Second, the overall stability of the attachment increases as multiple linkages are formed between the oligonucleotide and the substrate which is independent of the approach used to bring the biomolecule into contact with the substrate.

The formation of multiple noncovalent complexes results in a higher overall stability of the complex between the oligonucleotide and the substrate allowing the use of low affinity complex builders for a stabile immobilization. Some of the frequently applied immobilization chemistries for oligonucleotides are reversible (e.g. the Schiff's base formation between amines and aldehydes) and require a subsequent stabilization step e.g. by reduction with $NaCNBH_3$. For these reversible reactions the immobilization via multiple linkages is beneficial since it leads in sum to a higher stability of the intermediates formed prior to the stabilization reaction. In some cases the gain in stability is great enough that the stabilization reaction becomes unnecessary.

Third, the use of oligonucleotides with multiple attachment sites allows the production of substrates with higher oligonucleotide loading. Usually the reactive sites on the substrate are in large excess to the oligonucleotides and the improved attachment due to multiple attachment moieties can lead to better use of the available sites on the substrate.

In another embodiment, the multiplicity of reactive binding moieties provided on the biomolecules may allow the biomolecules to bind, either in a covalent or a noncovalent manner, to the substrate surface. With respect to noncovalent binding, the multiplicity of binding moieties may comprise chemical moieties such as biotin, streptavidin, phenyl boronic acid (PBA), and salicyl hydroxamic acid (SHA). With respect to covalent binding, the multiplicity of binding moieties may comprise the use of reactive hydrazide structures. Such structures may be either branched or unbranched thereby allowing for great versatility in the level of possible binding moieties available. Thus, not only are the biomolecules provided with dendritic branching structures, but the reactive binding moieties themselves may also be branched such that each branch has a reactive hydrazide element for use in binding the biomolecule to a substrate surface.

In another embodiment, the multiplicity of binding moieties on the biomolecule provides a means whereby biomolecules attached to a substrate surface comprising an electronically addressable microchip are protected from inadvertent removal from the attachment site on the microchip caused by high voltage and current resulting from electronic biasing of the microchip electrode. Thus, in a preferred embodiment, the multiple attachment scheme of the current invention provides for binding of biomolecules to the substrate capable of withstanding current densities of at least 4 mA/cm$^2$.

In still another embodiment, the invention provides for a method of adding reactive binding moieties to the dendritic structures attached to the biomolecules such that the addition may occur in a single reaction step.

In still another embodiment, the invention provides a composition of matter comprising new chemical modifications of oligonucleotides containing one or multiple hydrazides and thereby the building blocks (e.g. phosphoramidites) for the generation of modified oligonucleotides thereof. These hydrazides comprise reactive groups and can be used for the conjugation of oligonucleotides to fluorophores or other small molecules, to peptides, proteins or antibodies, or to substrate surfaces.

In still another embodiment the attachment scheme can be applied to surface synthesis of biomolecules and analytical applications requiring surface immobilization of compounds.

BRIEF DESCRIPTION OF THE DRAWINGS

FIG. 9C shows a scheme wherein the hydrazide-labeled oligonucleotide can react with an activated-ester monomer and used to form a substrate for immobilization of biomolecules.

FIG. 25B are the actual fluorescent photoimages of the oligomers bound to the glass slide, their binding levels are displayed graphically in FIG. 25A.

FIG. 26B are the actual fluorescent photoimages of the oligomers bound to the glass slide, their binding levels are displayed graphically in FIG. 26A.

DETAILED DESCRIPTION OF THE PREFERRED EMBODIMENTS

Figure 1:
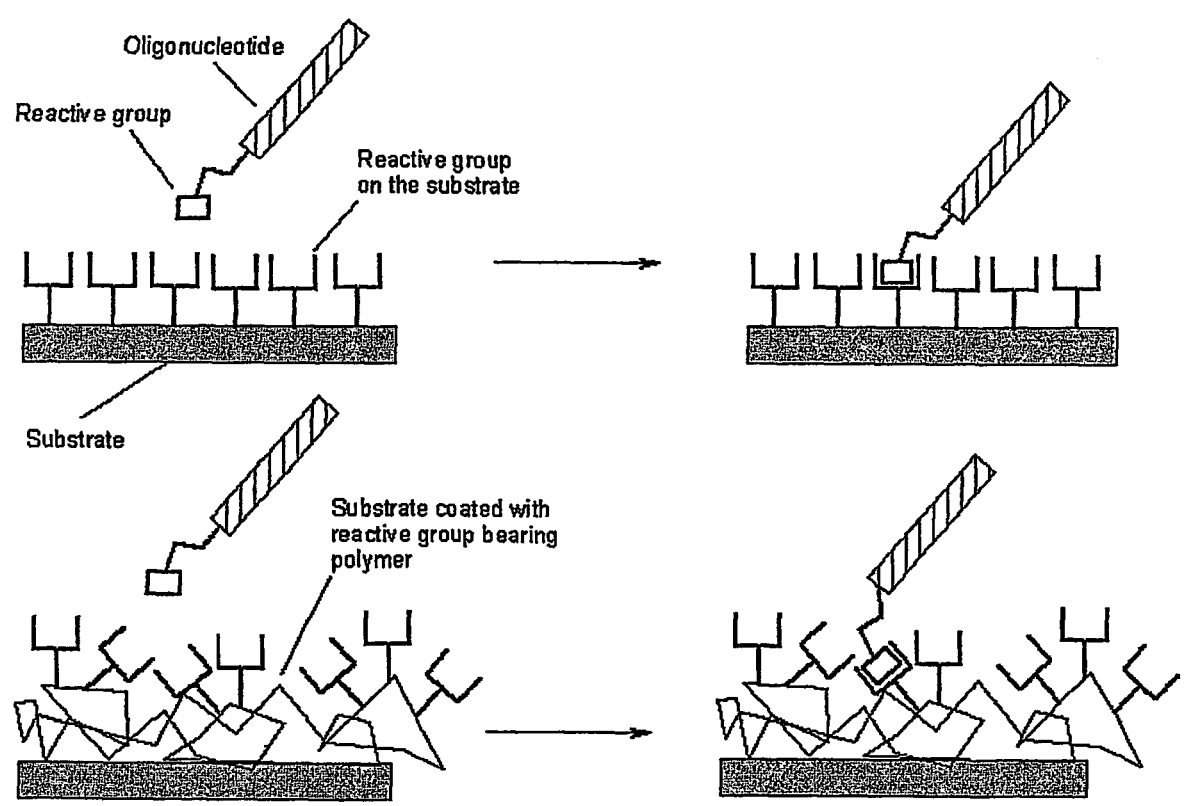
FIG. 1 is a schematic depicting the classic approach for immobilizing oligonucleotides on planar substrates. Generally, a single reactive group is used to bind the oligomer to the substrate surface.

Referring now to the specific embodiments of the invention, biomolecules are provided having a multiplicity of substrate surface binding moieties.

By "biomolecule" is meant a biologically relevant molecule that is used to contact molecular entities in a test sample. Generally, these include, at least in part, molecules such as nucleic acids, including a single nucleic acid, oligonucleotides and polynucleotides, DNAs, RNAs, CNAs (cyclohexyl nucleic acids), p-MeNAs (methyl or methoxy phosphate nucleic acids), proteins, peptides, enzymes, and antibodies attached to chemical moieties for binding the biomolecule to a substrate surface. Biomolecules also include unnatural or synthetic molecules structurally derived from the naturally occurring molecules such as peptide nucleic acids (PNAs) or p-RNAs (pyranosyl RNAs) attached to chemical moieties for binding the biomolecule to a substrate surface. Having such a binding moiety, biomolecules may also be referred to as "derivatized biomolecules". Such biomolecules therefore also include oligonucleotides containing oxidized ribose, amine terminations, or any entity of the well known bioconjugate pairs as outlined by Hermanson (Hermanson, G. T. *Bioconjugate Techniques* copyright 1996, Academic Press, San Diego, Calif.) herein incorporated by reference, and/or alternative nucleic acid structures such as pRNAs (in reference to pRNAs as described in co-pending application Ser. No. 09/374,338 filed Aug. 13, 1999 herein incorporated by reference). Generally, attachment of the chemical moieties to the biomolecules comprises a covalent bond. With respect to attachment of derivatized biomolecules to a substrate surface, such attachment may use either a covalent or a noncovalent bond.

By "polymer" is generally meant macromolecules assembled from the successive linkage of a large number of smaller molecules generally referred to as monomers as recognized by one skilled in the art (for a more detailed description see Odian, G. *Principles of Polymerization, Third Edition* copyright 1991 John Wiley and Sons Inc., New York, N.Y.). In a preferred embodiment, a homogeneous polymer may be composed of a single type of monomer, while a heterogeneous polymer is be composed of more than one type of monomer. In another preferred embodiment, formation of a polymer can be initiated by thermal decomposition of initiators (e.g. AIBN, benzoyl peroxide), photolytic cleavage of initiators (e.g. UV initiation of Daracur 4265), redox reactions (e.g. cerium (IV) sulfate), ionizing radiation (e.g. α, β, γ or X-rays), plasma initiation (e.g. Argon, Nitrogen, Oxygen), or electrolytic initiation using tetrabutylammonium perchlorate in which the polymerization occurs only over a preselected site using an electric current (Samal, S. K.; Nayak, B. *J. Polym. Sci. Polym. Chem. Ed.* 1988, 21, 1035.)

By "binding moiety" is generally meant any chemical moiety utilized in the generation of attachment of biomolecules to a substrate surface. A binding moiety may be contained on a biomolecule or contained on a substrate surface. Table 1 Binding Moieties provides a list of binding moieties used.

TABLE 1

Binding Moieties

| Structure | Functional Group or Chemical Name |
|---|---|
| 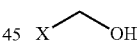 | Alcohol |
| 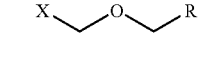 | Ether |
| 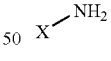 | Primary amine |
| 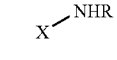 | Substituted amine |
| 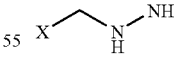 | Hydrazine |
| 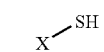 | Sulfhydryl |
| 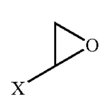 | Epoxide |
| 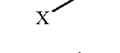 | Aziridine |

TABLE 1-continued

Binding Moieties

| Structure | Functional Group or Chemical Name |
|---|---|
| R-CH=CH-X; R = C, N, O, P, S | Vinyl |
| CH2=CH-CH2-R-X; R = C, N, O, P, S | Allyl |
| X-C(=O)-H | Aldehyde |
| R-C(=O)-X | Ketone |
| X-CH(O-R)(O-R) | Acetal |
| R-S-S-X | disulfide |
| X-CH2-C(=O)-OR | Ester |
| X-CH2-C(=O)-OH | Carboxylic Acid |
| X-CH2-C(=O)-NH2 | Amide |
| X-CH2-C(=O)-NH-R | Monosubstituted Amide |
| X-CH2-C(=O)-N(R)(R1) | Disubstituted Amide |
| X-NH-C(=O)-CH2-Y; Y = Br, I | Bromo- or Iodo-acetamide |
| X-C(=O)-NH-NH2 | Hydrazide |
| R-S-C(=O)-X | Thioester |
| N-hydroxysuccinimidyl ester structure; Y = H, SO3Na | (sulfonated)-N-Hydroxy succinimidyl ester |
| Azlactone structure | Azlactone, an activated ester |
| X-N=C=O | Isocyanate |
| X-N=C=S | Isothiocyanate |
| X-C(=O)-N2+ | Acyl azide |
| X-O-C(=O)-O-R | Carbonates |
| R3-O-P(O-R2)(N(R)(R1)) | phosphoramidites |

Symbols:
X = a biomolecule or substrate/solid support;
R, $R_1$, $R_2$, $R_3$ = organic carbon moieties unless otherwise indicated.

By "Lewis Base" is generally meant any chemical moiety capable of donating a pair of electrons to an electron deficient center. In a preferred embodiment, a Lewis Base is more specifically referred to as a "nucleophile" in which a reactive center donates a pair of electrons to carbon resulting in a covalent bond between the reactive center and the carbon as recognized by one skilled in the art (For an expanded definition see: Smith, M. B. *Organic Synthesis* copyright 1994 McGraw Hill Inc., New York, N.Y., or any organic chemistry textbook).

By "Lewis acid" is generally meant any electron deficient chemical moiety capable of receiving a pair of electrons. By "electrophiile" is generally meant the specific case in which the Lewis Acid is carbon, as recognized by one skilled in the art (For an expanded definition see: Smith, M. B. *Organic Synthesis* copyright 1994 McGraw Hill Inc., New York, N.Y., or any organic chemistry textbook). In a preferred embodiment, as an example, salicylic hydroxamic acid is capable of acting as a Lewis base donating a pair of electrons to boron, a Lewis acid, of phenyl boronic acid resulting in a noncovalent linkage. In yet another preferred embodiment, as an example, hydrazide is capable of acting as a nucleophile donating a pair of electrons to the reactive carbon center of an NHS ester, an electrophile, forming a covalent linkage to said carbon center.

By "branched linking moiety" is generally meant any chemical species which is capable of coupling through a specific reactive moiety to a biomolecule and is also capable of further attachment to more than one molecule through alternative reactive centers. In a preferred embodiment, a branched linking moiety is a phosphoramidite of which examples are shown in Table 2, Entries 1–4. In these examples, the phosphorus acts as the reactive moiety while the esters of entries 1, 2, and 3 and the protected alcohols of 4 are alternative reactive centers.

By "branched linking structure" is generally meant a biomolecule resulting from treatment of a biomolecule with a branched linking moiety. The alternative reactive centers of the branched linking moiety are now contained within the branched linking structure. In a preferred embodiment, as an example, a branched linking structure is represented by entry 5 of Table 2 in which the biomolecule shown is the result of treating a biomolecule with a branched linking moiety, specifically the compound displayed in entry 4 of Table 2. In another preferred embodiment the branching linking structure is capable of being combined in a homogeneous series in which a biomolecule is modified with a branching linking moiety, which in turn is further modified by the same branched linking moiety through the alternative reactive centers of the resultant branched linking structure, generating a new branched linking structure. This construction of larger branched linking structures by means of a series of linkages of a branched linking moiety can be further continued as shown in Table 2, Entries 6–8 In yet another embodiment, the branching linking moieties are capable of being combined in a heterogeneous series in which a biomolecule is modified with a branching linking moiety, which in turn is further modified by a different branched linking moiety through the alternative reactive centers of the initial branched linking moiety, generating a new branched liking structure. This construction of larger branched linking structures by means of a series of linkages of branched linking moieties can be further continued as shown in Table 2, Entries 9–12.

TABLE 2

Branched Linking Moieties and Branched Linking Structures

| Entry | Chemical Structure | Name or class of compound |
|---|---|---|
| 1 | 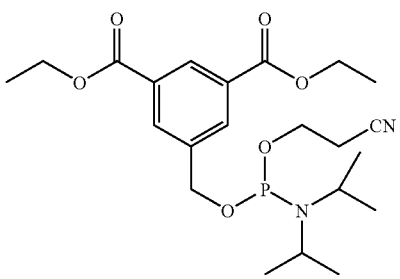 | Branched Linking Moiety: Diethyl 5-{[(2-cyanoethoxy)-(diisopropylamino)-phosphanyloxy]methyl}-isophthalate; Compound 1c; a diester phosphoramidite |
| 2 | 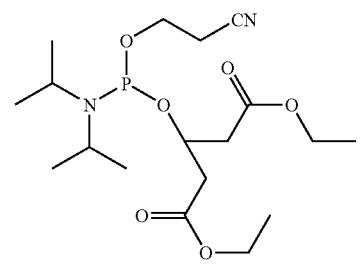 | Branched Linking Moiety: Diethyl 3-[(2-cyanoethoxy)-(diisopropylamino)-phosphanyloxy]glutarate; a branched diester phosphoramidite. |
| 3 | 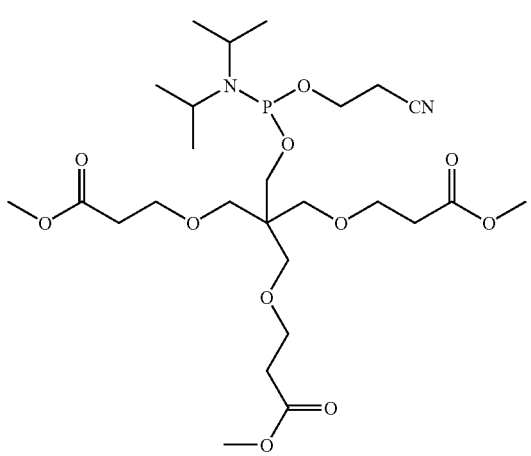 | Branched Linking Moiety: Dimethyl 3,3'-(2-{[(2-cyanoethoxy)(diisopropylamino)phosphanyloxy]-methyl}-2-{[2-(methoxycarbonyl)ethoxy]methyl}-propane-1,3-diylbisoxy)-dipropionate; Compound 1d; a tri-ester phosphoramidite |

TABLE 2-continued

Branched Linking Moieties and Branched Linking Structures

| Entry | Chemical Structure | Name or class of compound |
|---|---|---|
| 4 | 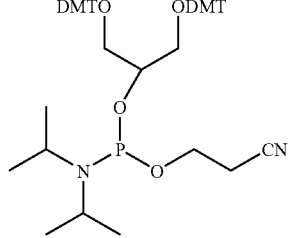 | Branched Linking Moiety: 1,3-bis-((di p-methoxy-phenyl)phenylmethoxy)-2-propyl O-2-cyanoethyl-N,N-diisopropylamino-phosphoramidite; a symmetrically branched phosphoramidite. DMT = di-(p-methoxy-phenyl)phenylmethyl |
| 5 | 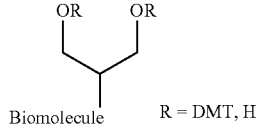 | First generation branched linking structure in which the alternative reactive species is an alcohol (R = H) or a protected alcohol (R = DMT). |
| 6 | 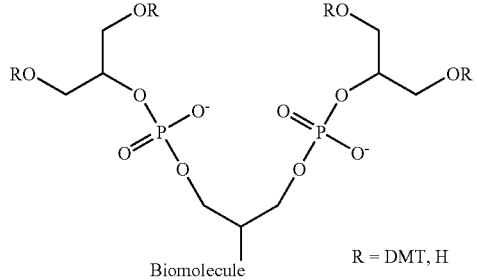 | Second generation homogeneous branched linking structure in which the alternative reacting species is an alcohol (R = H) or a protected alcohol (R = DMT). |
| 7 | 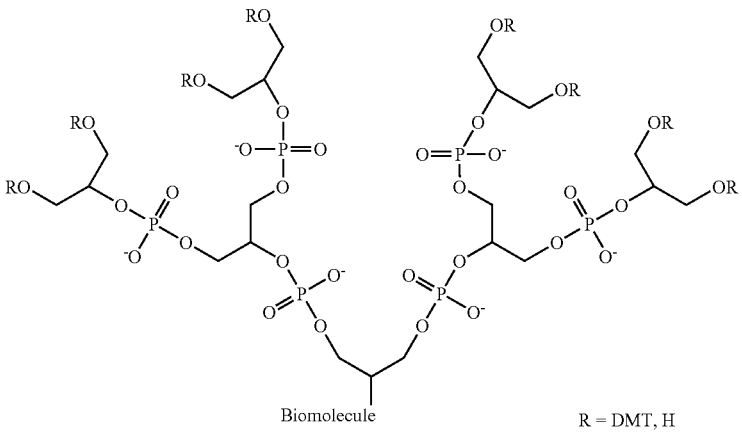 | Third generation homogeneous branched linking structure in which the alternative reacting species is an alcohol (R = H) or a protected alcohol (R = DMT). |

TABLE 2-continued

Branched Linking Moieties and Branched Linking Structures

| Entry | Chemical Structure | Name or class of compound |
|---|---|---|
| 8 | 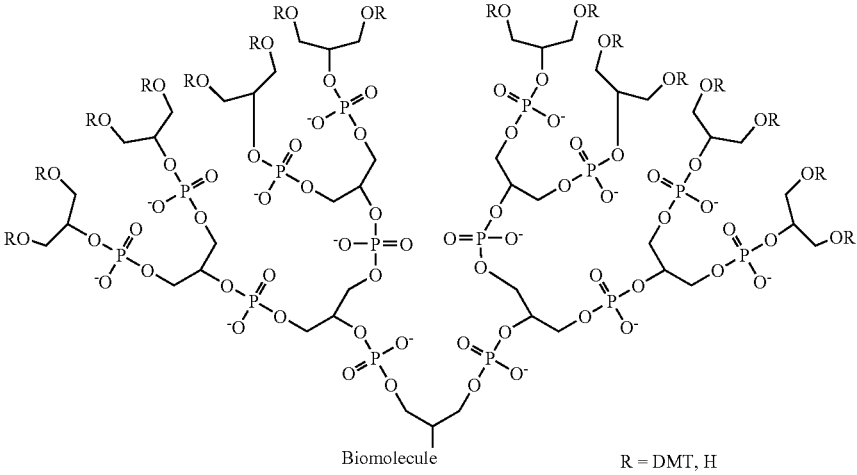 | Fourth generation homogeneous branched linking structure in which the alternative reacting species is an alcohol (R = H) or a protected alcohol (R = DMT). |
| 9 | 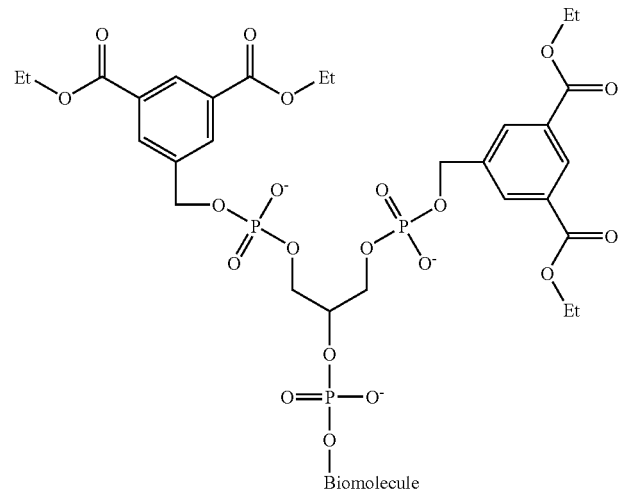 | Second generation heterogeneous branched linking structure. |
| 10 | 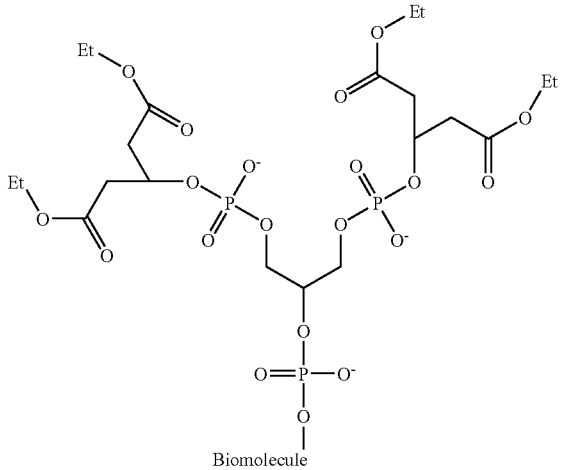 | Second generation heterogeneous branched linking structure. |

TABLE 2-continued
Branched Linking Moieties and Branched Linking Structures
| Entry | Chemical Structure | Name or class of compound |
|---|---|---|
| 11 | 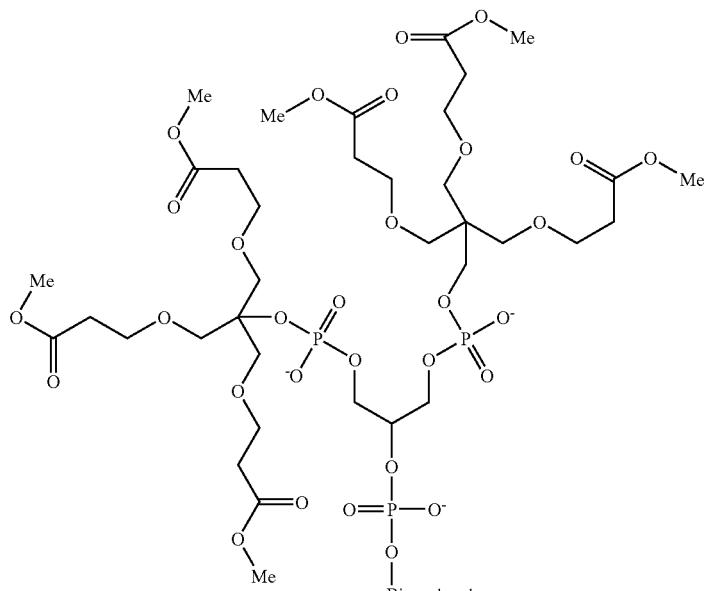 | Second generation heterogeneous branched linking structure. |
| 12. | 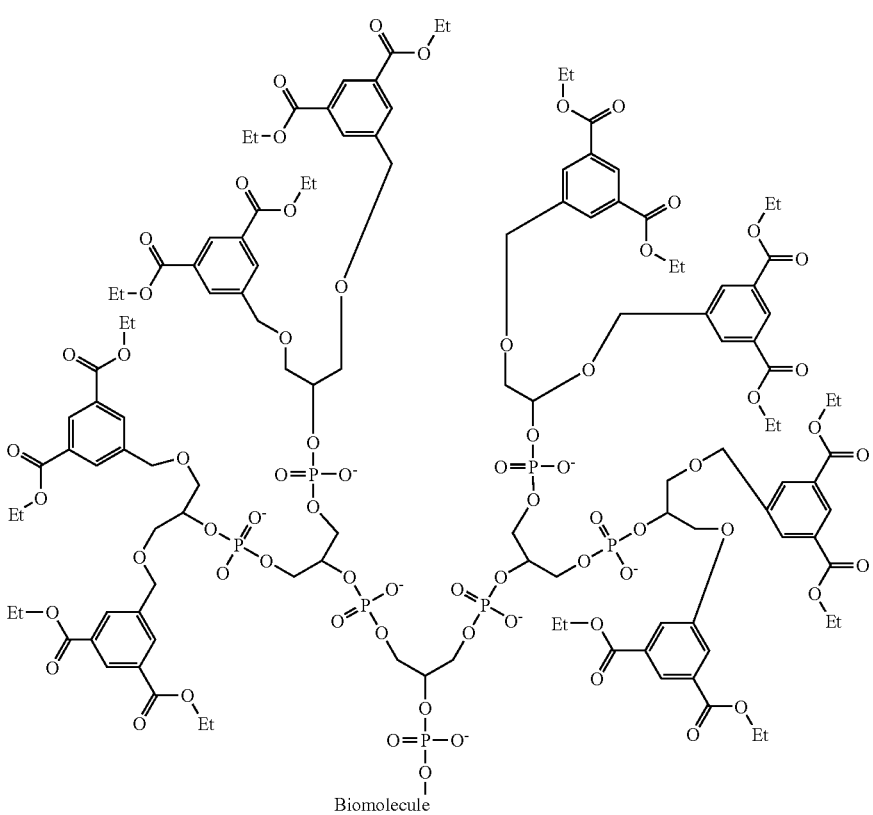 | Third generation heterogeneous branched linking structure. |

By "substrate" is generally meant any material whose surface contains moieties with which the multiple reactive binding moieties of the biomolecules may couple. This substrate can be, among others, a glass slide, a functionalized glass slide, a chemically activated microchip surface, a surface covered with a single or multiple layers of reactive molecules, or a surface covered with a polymer having moieties with which the multiple reactive binding moieties of the biomolecules may react. In a preferred embodiment, a substrate surface is a permeation layer of an electronically addressable microchip. In a preferred embodiment, the functional, chemically active, or reactive moieties of a substrate are selected from (but not limited to) the functional groups listed in Table 1.

By "precursor" is generally meant any reactive moiety which can be transformed to an alternative reactive moiety with treatment of one or more chemical reagents. In a preferred embodiment, as an example, the three ester moieties of 1d, (Entry 3 of Table 2) are precursors to hydrazides. They are transformed to a hydrazide moiety with the treatment of hydrazine.

Figure 9A:
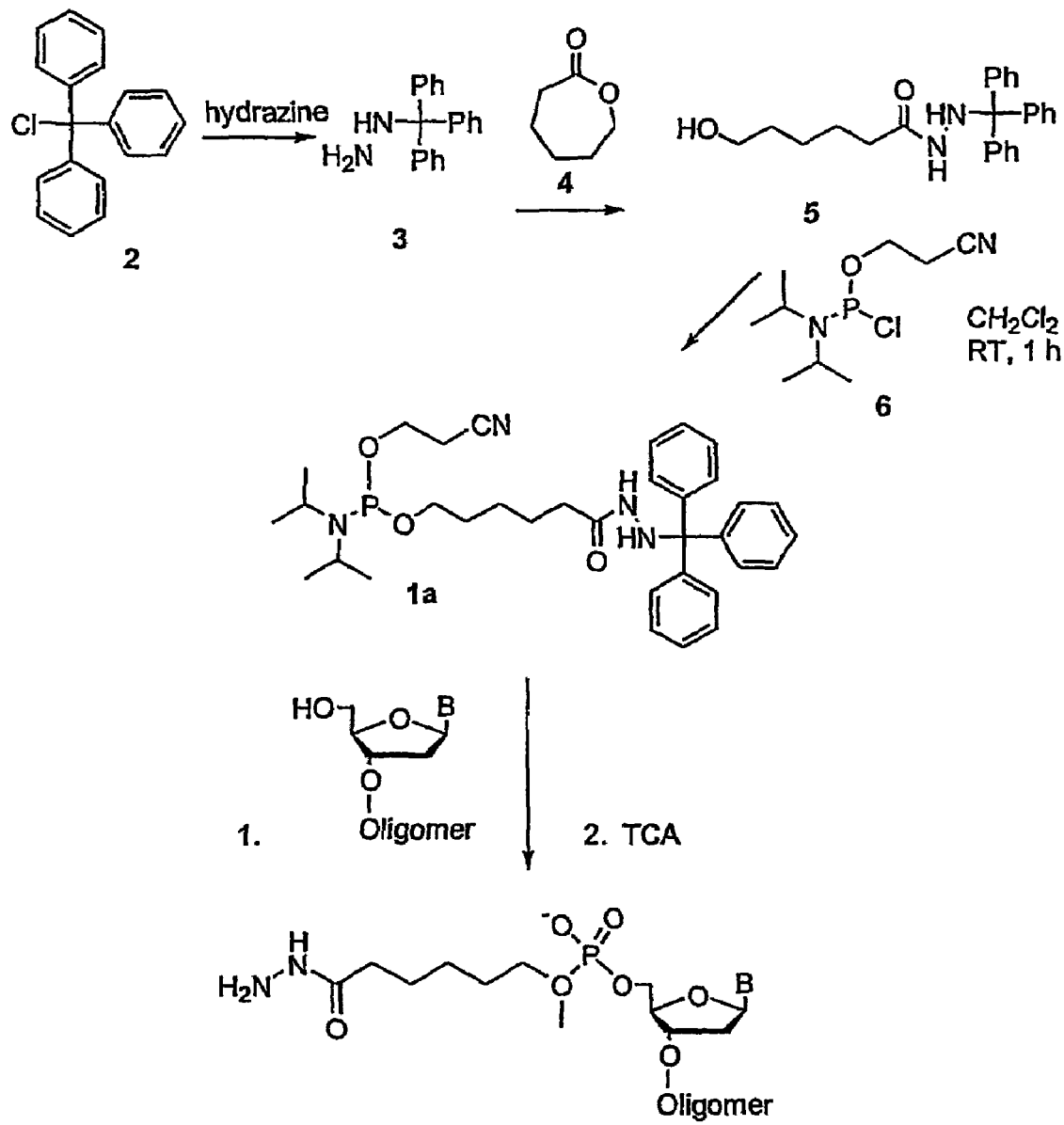
FIGS. 9A–C show three schemes of which A and B show steps for making a novel phosphoramidite for incorporation into an oligonucleotide biomolecule.

By "protected" is generally meant blocking the reactivity of a reactive moiety with one or more reagents while a chemical reaction can be carried out at an alternative reactive site of the same compound without obstruction or complication from the initial reactive moiety. Upon completion of the transformation at the alternative reactive site the protecting group of the reactive moiety can be removed, unblocking the reactive center. In a preferred embodiment, a protected moiety is a specific type of precursor. In yet another preferred embodiment, as an example, the hydrazide moiety of 1a of FIG. 9A is protected with a trityl group. Upon addition of 1a to a biomolecule the trityl group is chemically removed deprotecting the hydrazide functionality.

By "activatable" is generally meant any functional group which is capable of undergoing a transformation to a reactive moiety when treated with one or more chemical reagents. By "activated" is meant a functional group which has undergone such a transformation to a reactive moiety. In a preferred embodiment, an activatable moiety can be a protected moiety or a precursor. In yet another preferred embodiment, the functional group is generally considered benign, unreactive, or incapable of binding to a substrate or biomolecule. Upon treatment with one or more chemical reagents, the functional group is transformed to a moiety capable of binding to a substrate or biomolecule. In a preferred embodiment, as an example, the ester groups of the compounds listed in Table 2 Entries 1–3 are transformed to hydrazides with treatment with hydrazine. In yet another preferred embodiment, as an example, a substrate containing acetal groups is generally considered to be unreactive. Upon treatment with an acidic source, the acetals are transformed to aldehydes which are capable of binding to hydrazide modified biomolecules.

By "microarray" is generally meant a geometric arrangement of a plurality of locations containing defined biomolecules, such individual locations being restricted to linear dimensions of 1 mm or less. Microarrays include an electronically addressable microarray such as an array designated the "APEX chip" as in U.S. Pat. No. 5,632,957 herein incorporated by reference.

Figure 2:
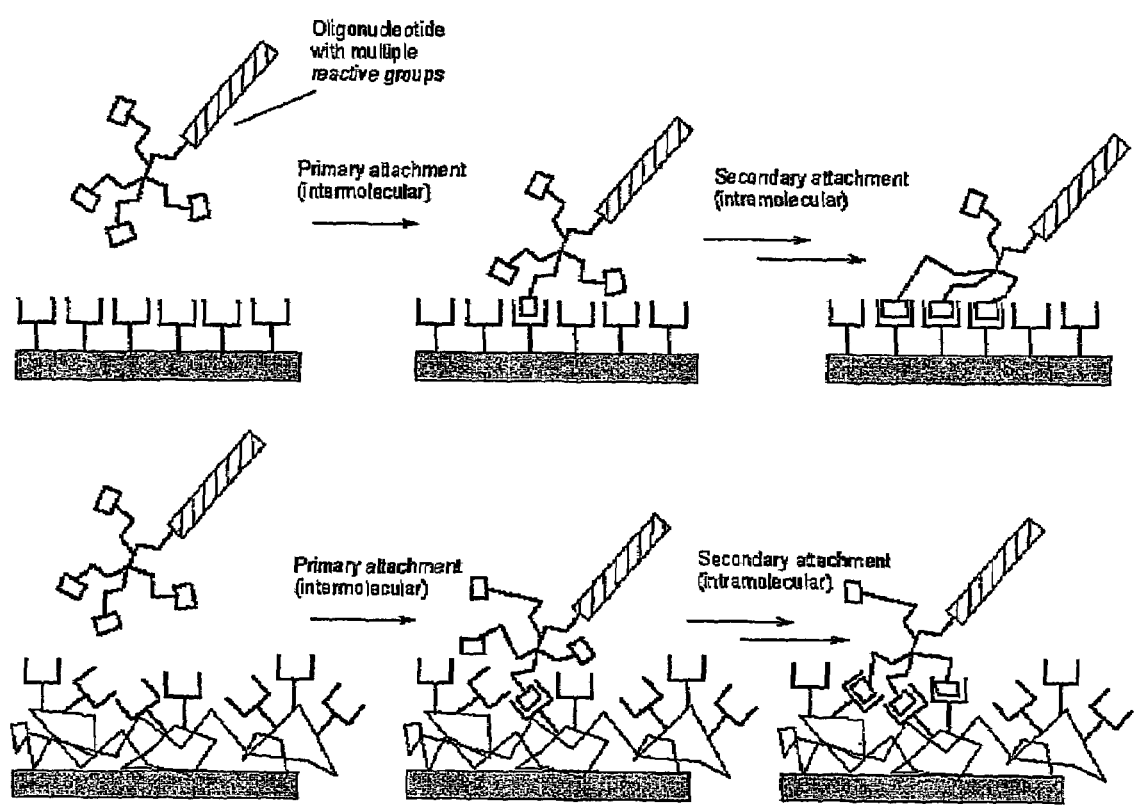
FIG. 2 is a schematic depiction of the immobilization approach of the invention wherein the biomolecule has a multiplicity of attachment or binding moieties that can participate in the covalent or noncovalent binding of the biomolecule to the substrate.
Figure 3:
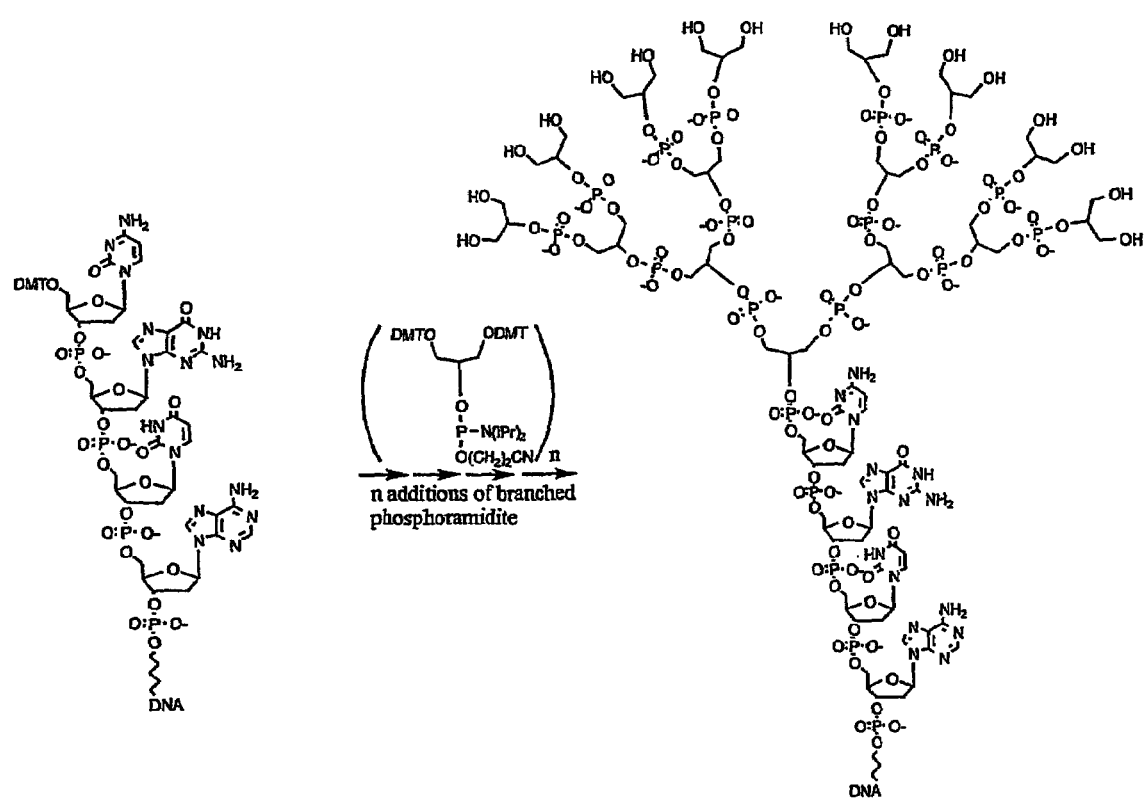
FIG. 3 is a more detailed view of one example of a nucleic acid strand attached to a multiplicity of reactive moieties for binding to a substrate surface. In this example, the chemical structures of branched phosphoramidites are added in multiple fashion to create a dendrimeric structure attached to the biomolecule.

FIG. 2 shows a basic schematic for the scheme of the invention wherein biomolecules are bound to a substrate surface through a multiplicity of attachment moieties. The multiples of attachment moieties may be provided to a biomolecule using the following methods. Each of these approaches is compatible with standard solid phase synthesis of biomolecules comprising oligonucleotides.

1. Preparation of Oligonucleotides with Multiple Attachment Sites 1.1 Oligonucleotide Synthesis with Branching Phosphoramidites:

Branched biomolecule (e.g. oligonucleotides) structures having branched phosphoramidites are commercially available (Chemgenes, Ashland, Mass.; Glenn Research, Sterling, Va.). After one or more consecutive couplings of such branching amidites in the solid-phase oligonucleotide synthesis (FIGS. 5A and B), oligonucleotides with two or more terminal hydroxyl groups are generated. Any other building block introducing branches into the oligonucleotide can be applied here in a similar manner. These hydroxyl groups can be reacted with a second type of phosphoramidite to generate the reactive group (i.e. the binding moiety) for the attachment of the biomolecule to the substrate. This phosphoramidite can be chosen from several available amidites such as biotin amidites (e.g. Glenn Research, Cat No. 10595002), amino modifiers (e.g. Glenn Research, Cat. No. 10190602), thiol modifiers (e.g. Glenn Research, Cat. No. 10192602), phenylboronic acid amidites (Prolinx, Bothell, Wash.) and others. Further, phosphoramidites containing hydrazides in a protected or precursor form (FIG. 9A) can be used. The result is an oligonucleotide having two or more (preferably 2 to 8) reactive groups.

Figure 6A:
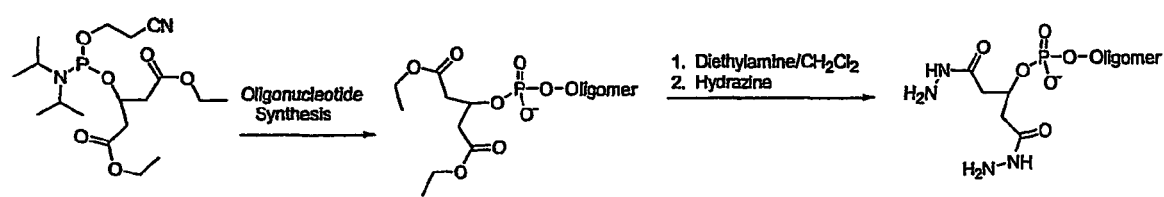
FIGS. 6A–C illustrate synthetic steps using phosphoramidites to produce biomolecules having multiple reactive sites. These moieties contain ester groups that are converted into hydrazides during the deprotection of the oligonucleotides with hydrazine.
Figure 6B:
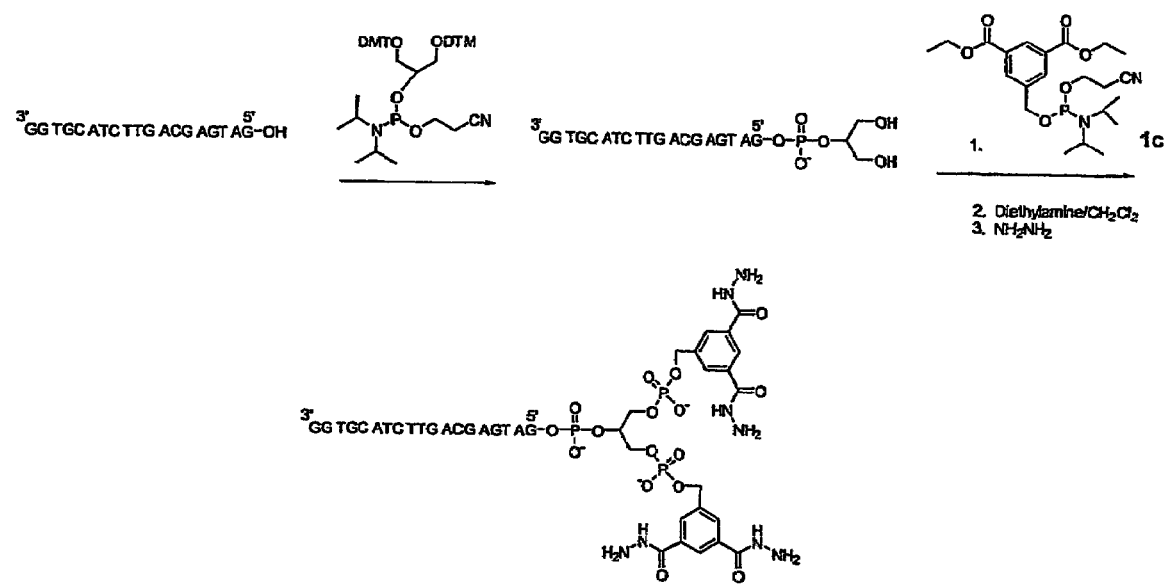
Figure 6C:
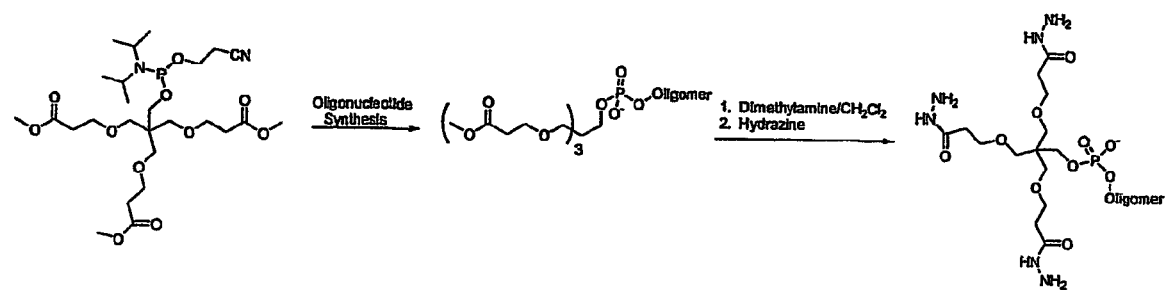
Figure 7:
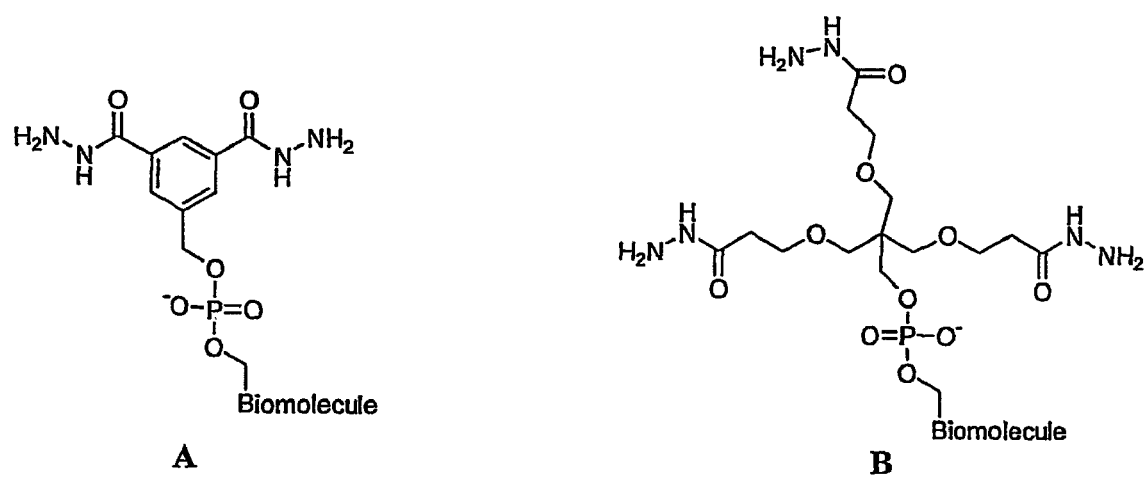
FIG. 7 shows chemical structures A and B comprising biomolecules having direct attachment of hydrazide moieties for use in immobilizing the biomolecule through a covalent bond to the substrate.

1.2 Direct Introduction of Synthons Having More than One Reactive Group for Attachment:

Alternatively, biomolecules with multiple attachment sites can be obtained by the coupling of special phosphoramidites. These amidites can contain in a protected or precursor form more than one reactive group for the immobilization at the substrate. The reactive group in branched amidites can be again one of the known functionalities such as amino groups, thiols, aldehydes, or hydrazides. Examples for such amidites are shown in FIGS. 6A–C.

Figure 8A:
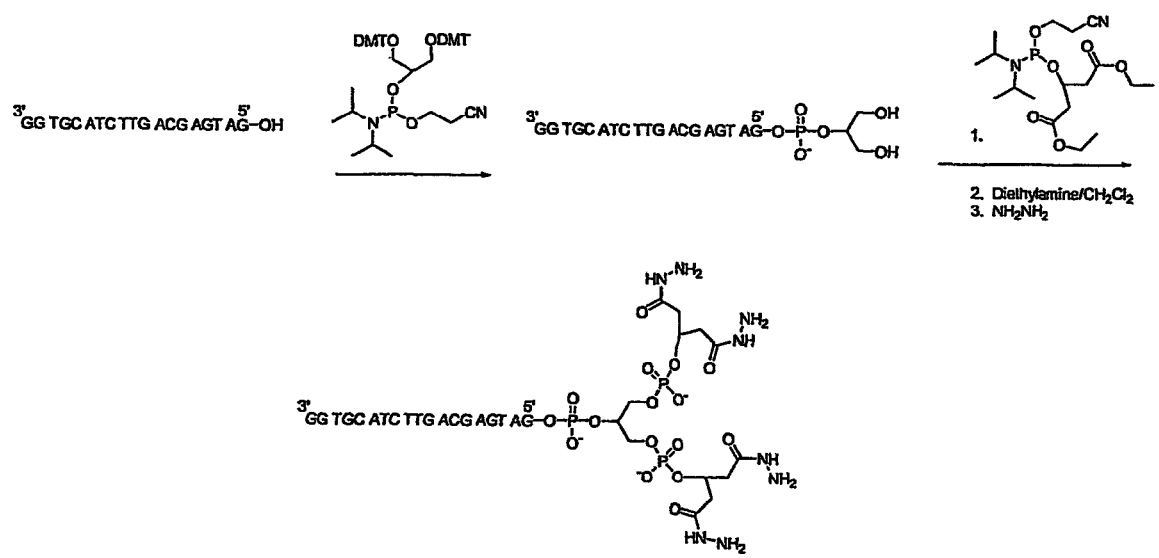
FIGS. 8A–D show chemical syntheses to produce structures having multiple binding moieties. In (A) a branched phosphoramidite is added to an oligonucleotide which is further modified with a bifunctional phosphoramidite followed by deprotection with of diethylamine/CH2Cl2 and hydrazine to generate a binding moiety having four hydrazide groups for binding a substrate. In (B) a reaction scheme similar to (A) is provided resulting in six hydrazide binding moieties. In (C) the sequential use of two different branched phosphoranidites results in 16 hydrazide binding moieties per biomolecule. In (D) a branched phosphoramidite is used in two steps to form a dendrimeric structure followed by a phosphoramidite and hydrazine treatment to result in 4 hydrazide binding moieties per biomolecule.
Figure 8B:
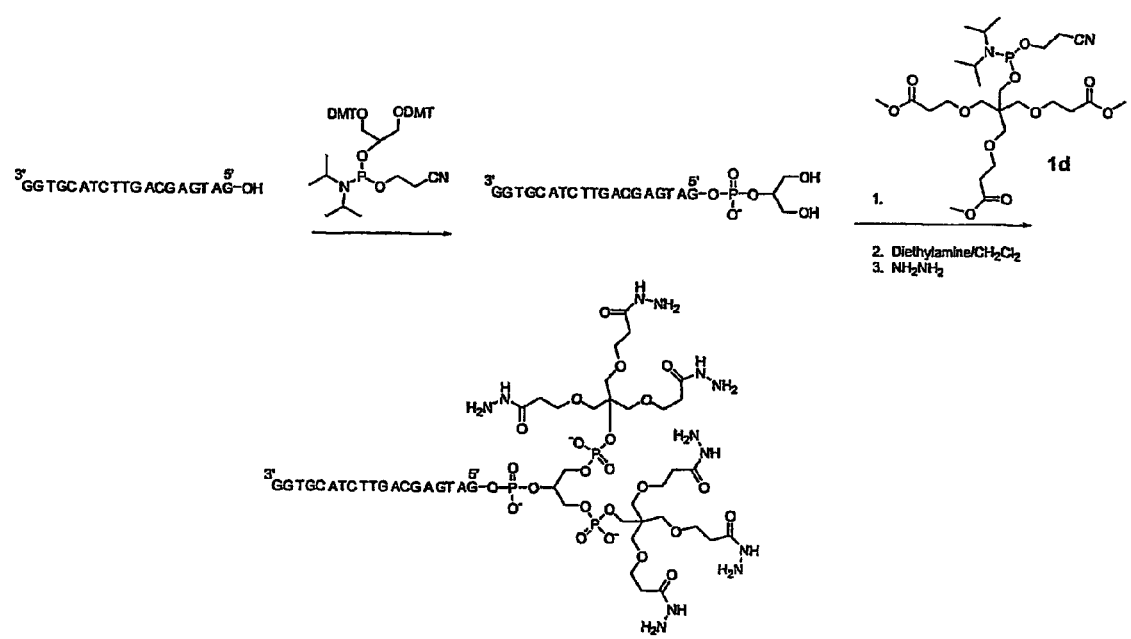
Figure 8C:
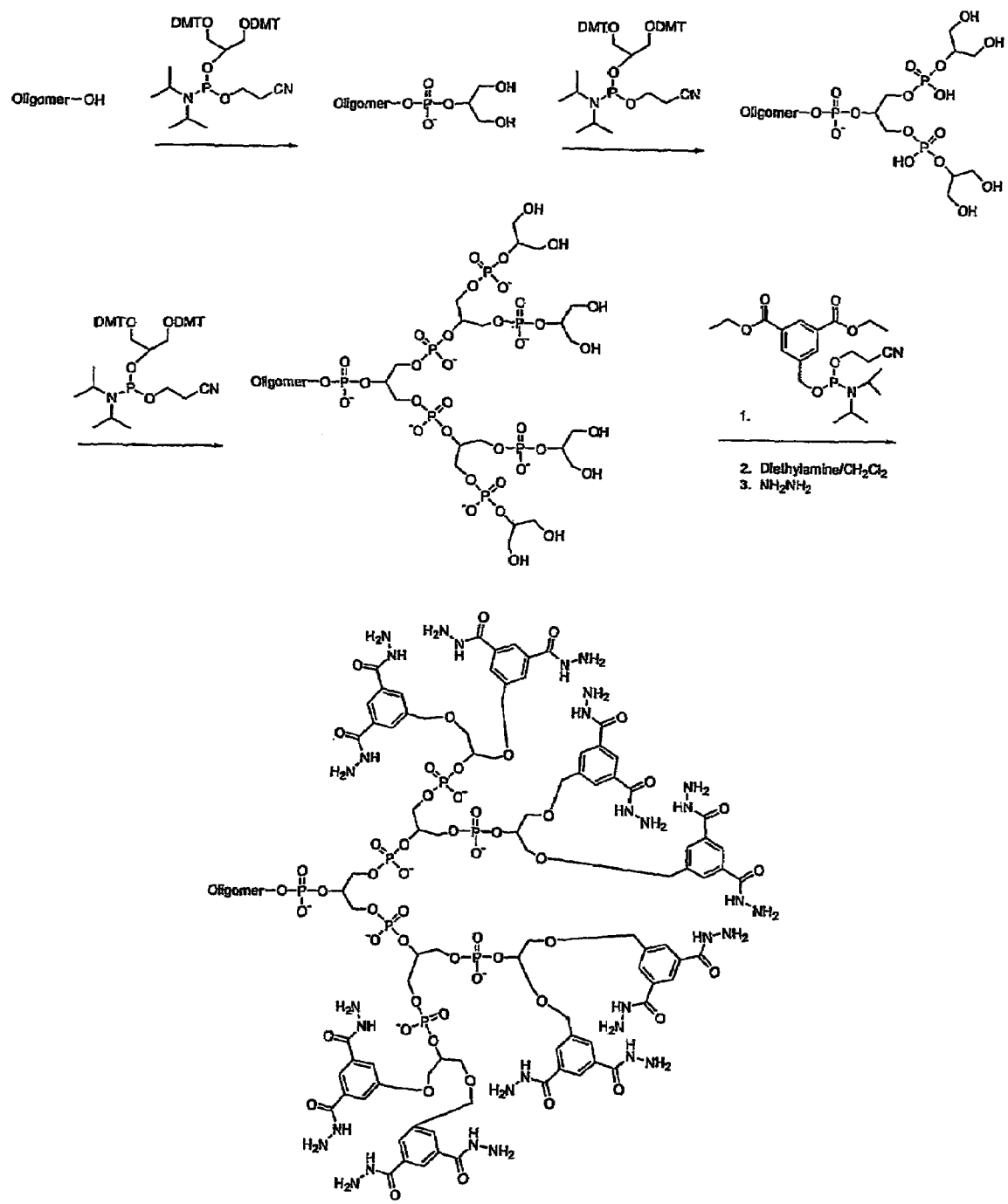
Figure 8D:
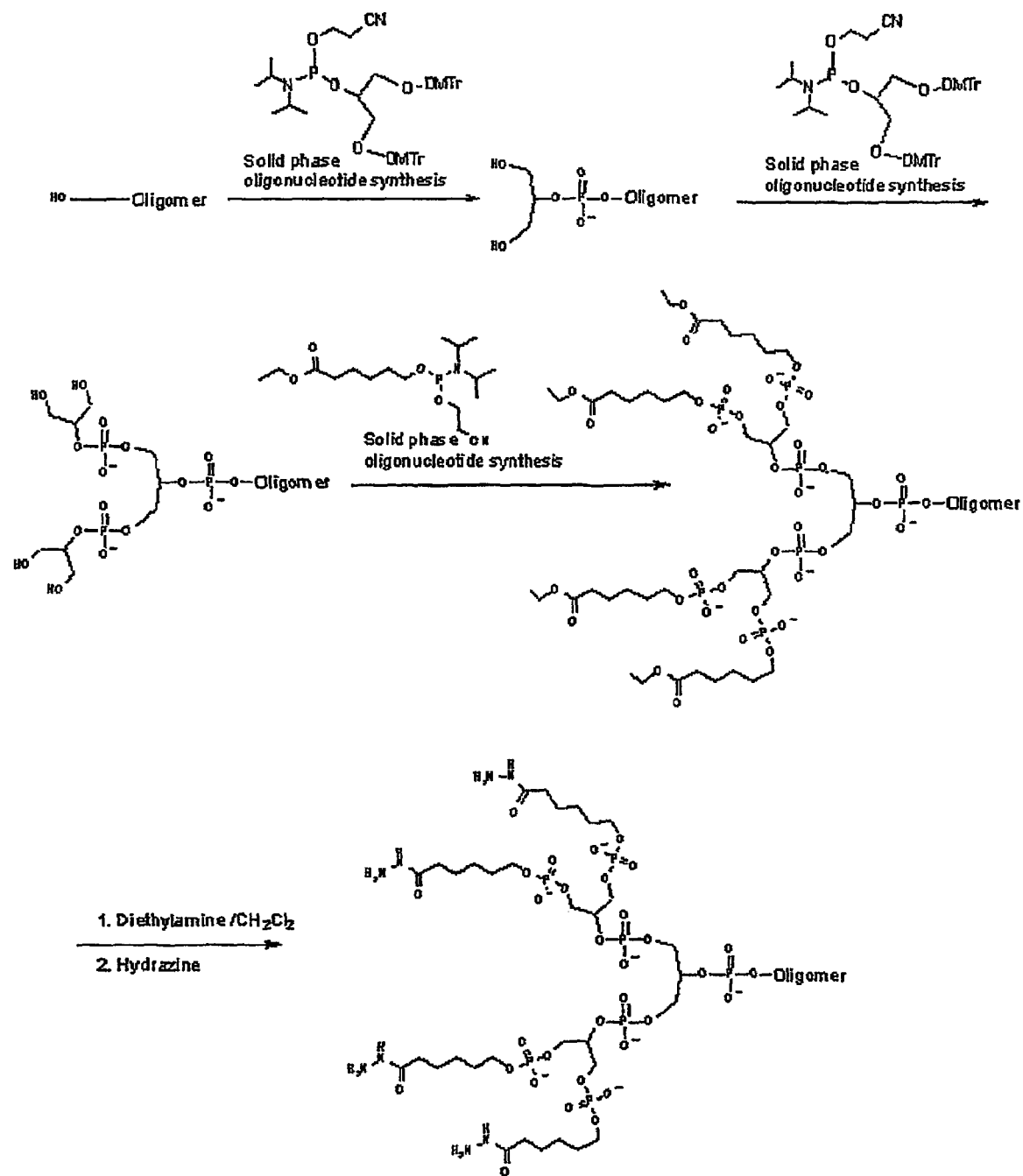

1.3 Combined Approach:

A third approach for the synthesis of biomolecules with multiple reactive groups is the combination of the coupling of branching amidites and amidites with multiple reactive sites (FIGS. 8A–C).

In a particularly preferred embodiment, biomolecules are provided having a tethered hydrazide for attachment to a substrate surface through a covalent bond. In this embodiment, NHS and Sulfo-NHS and other moieties may be used as a means of activating a substrate or any other type of biomolecule and coupling to biomolecules or even solid surfaces. In the application of the present invention, such attachment provides a novel means whereby biomolecule attachment may be carried out and provide for resistance against damage to tethered biomolecules caused by the extreme reaction conditions associated with electronic addressing of an electronic microchip. Thus, the hydrazide chemistry and multiple attachment scheme of the present invention fulfills requirements for survivability in the environment of an electronic system which requirements include a need for water solubility of the biomolecule, stability to water of the biomolecule and its coupling pair on the immobilizing substrate, and functionality to a pH of approximately pH 4.

The methods by which hydrazide binding moieties were added and utilized in the present invention are provided in the following examples. These examples show site specific covalent attachment of a biomolecule comprising an oligonucleotide in which attachment is accomplished with electronic concentration of a hydrazide-modified oligo onto an N-hydroxysuccinimidyl (NHS) modified polyacrylamide permeation layer above an electronically addressable microarray. The hydrazide moiety of the oligomer displaces the NHS ester forming a bishydrazide linkage. These examples therefore show 1.) Synthesis of the novel hydrazide phosphoramidite (e.g., compound 1) as shown in Example 1 (FIG. 9) and successful incorporation of these amidites onto synthetic oligomers using standard synthetic procedures; 2.) Preparation of N-Hydroxy- or N-hydroxysulfo-succinimidyl modified permeation layer; and 3.) A two-layer permeation layer above the electronically addressable microarray in which the activated monomers are incorporated into only the top layer.

Unless otherwise indicated, all reactions were magnetically stirred. Reagents were obtained in analytical grade from Aldrich Chemical Company (Milwaukee Wis.) and solvents from Riedel. Column Chromatography is accomplished using silica gel 60 Merck, 230–400 mesh). Melting points are uncorrected. IR Spectra are measured on a Perkin Elmer Paragon 1000 FT-IR equipped with a Graseby Specac 10500 AIR unit. $^1$H-NMR spectra are recorded at 400 MHz; $^{13}$C spectra at 100 MHz and $^{31}$P at 162 MHz with a Bruker DRX 400 spectrometer. $^1$H chemical shifts are reported in units of δ using TMS as internal standard, and coupling constants are reported in units of Hz. ESI Mass spectra are recorded on a Finnigan LCQ instrument in negative ionization mode.

EXAMPLE 1

Experiment 1.1 Synthesis of N-Triphenylmethyl-6-hydroxycapronic acid hydrazide, (compound 5, FIG. 9A).

To a solution of 6.2 g (20 mmol) of tritylhydrazine hydrochloride (3a) in 200 ml of THF was added 2.22 g (22 mmol, 1.1 eq) triethylamine. The solution was stirred at room temperature (rt) for 15 min. filtered, concentrated to afford compound 3, then treated with 2.29 g (20 mmol, 1 eq) of ε-caprolactone (compound 4). The mixture is heated to 65° C. for 5 h the cooled to rt for 18 h. The precipitate was collected and recrystallized from ethyl acetate to afford 3.55 g (45%) of a white powder (compound 5):

$^1$H-NMR 7.49–7.47 (m, 5H), 7.35–7.10 (m, 10H), 6.55 (d, J=7.52, 1H), 5.55 (d, J=7.25, 1H), 3.54 (t, J=6.45, 2H), 1.87 (t, J=7.25, 2H), 1.62 (bs, 1H), 1.57–1.34 (m, 4H), 1.27–1.11 (m, 2H).

Experiment 1.2

Synthesis of 6-[(2Cyanoethoxy)(diisopropylamino) phosphanyloxy]-N'-tritylhexanohydrazide (compound 1a, FIG. 9A).

To a solution of 3.0 g (7.7 mmol) N-triphenylmethyl-6-hydroxycapronic hydrazide (compound 5) in 50 ml dry dichloromethane at rt was slowly added 4.0 g (31 mmol, 4 eq) of N-ethyldiisopropyl amine and 2.01 g (8.5 mmol, 1.1 eq) of chloro(diisopropylamino)-β-cyanoethoxyphosphine (compound 6) over 15 min. Upon complete addition, the reaction was stirred for 1 h, concentrated, and chromatographed (ethyl acetate/n-heptane 2/3 with 0.2% triethylamine) to afford 3.19 g (70%) of 1a as a pale yellow foam.

$^1$H-NMR, 7.49–7.46 (m, 5H), 7.34–7.20 (m, 10H), 6.57 (d, J=7.2, 1H), 5.57 (d, J=7.5, 1H), 3.85–3.74 (m, 2H), 3.62–3.48 (m, 2H), 2.62–2.59 (m, 2H), 1.88–1.84 (m, 2H), 1.53–1.33 (m, 4H), 1.27–1.13 (m, 14H); $^{31}$P-NMR (CDCl$_3$): δ=147.97.

Experiment 1.3

Figure 9B:
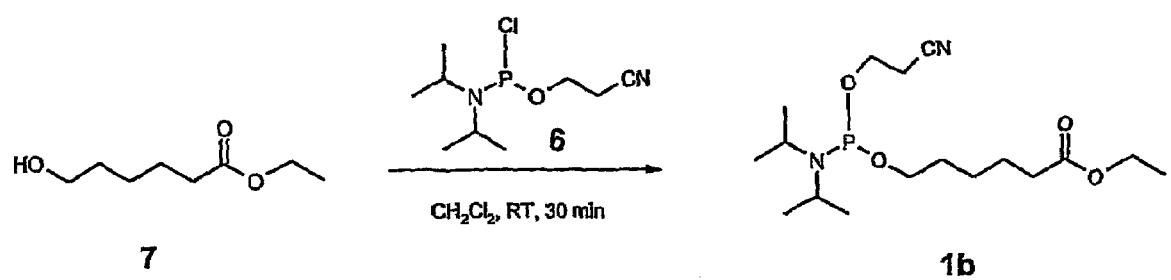
Figure 9C:
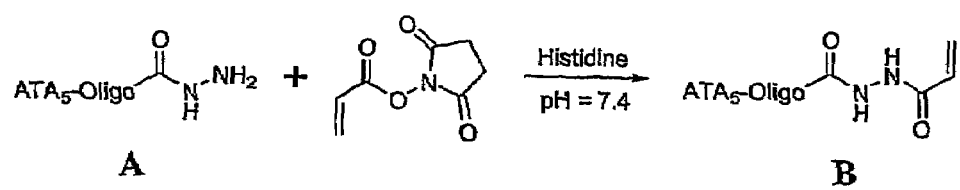

Preparation of Ethyl 6-[2-cyanoethoxy)(diisopropylamino)phosphanyloxy]hexanoate (compound 1b, FIG. 9B, Scheme 2).

To a solution of 1.65 g (10 mmol) of ethyl 6-hydroxyhexanoate (compound 7) in 30 ml dichloromethane at rt are slowly added 5.17 g (40 mmol, 4 eq) of N-ethyldiisopropyl amine and 2.6 g (11 mmol, 1.1 eq) of compound 6 over 15 min. Upon complete addition, the reaction was further stirred for 15 min, concentrated, and chromatographed (ethyl acetate/n-heptane ¼ with 0.2% triethylamine) to afford 2.47 g (69%) of compound 1b as clear oil: $^1$H-NMR 4.12 (q, J=7.25, 2H), 3.90–3.77 (a 21H), 3.75–3.55 (m, 41H), 2.64 (t, J=6.44, 21H), 2.30 (t, J=7.25, 21H), 1.69–1.59 (m, 4H), 1.44–1.34 (m, 2H), 1.25 (t, J 7.25, 3H), 1.20–1.12 (m, 12H); $^{31}$P-NMR (CDCl$_3$): δ=148.01.

Experiment 1.4

Preparation of ester phosphoramidite: Diethyl 5-{ [(2-cyanoethoxy)(diisopropylamino)phosphanyloxy] methyl}isophthalate (Compound 1c FIG. 6B)

To a solution of 1.29 g (5 mmol) diethyl 5-(hydroxymethyl)isophthalate [252.27] (98%, Aldrich; CAS 181425-91-2) in 20 ml dry dichloromethane at RT are added 2.59 g (40 mmol, 4 eq) N-ethyldiisopropyl amine [129.25] and 1.3 g (11 mmol, 1.1 eq) 2-cyanoethyl N,N-diisopropyl-chlorophosphoramidite [236.68] (Aldrich; CAS 89992-70-1) over 15 min with stirring. The mixture was concentrated and salts were precipitated with 30 mL ethyl acetate/n-heptane (2:3). The hydrochloride precipitate is filtered; the filtrate is concentrated and directly applied to a chromatography column. Elution with ethyl acetate/n-heptane (1:4) containing few drops triethylamine afforded 1.6 g (70%) 1c as a colorless oil. C$_{22}$H$_{33}$N$_2$O$_6$; $^1$H-NMR 8.59 (m, 1H, arom.), 8.21 (m, 2H, arom.), 4.87–4.75 (m, 2H, CH$_2$ cyanoethyl), 4.41 (q, J=6.98 Hz, 4H, CH$_2$ ethyl), 3.95–3.80 (m, 2H, 2× CH I—Pr), 3.74–3.61 (m, 2H, CH$_2$ cyanoethyl), 2.66 (t, J (P,H)=6.45 Hz, 2H, O—CH$_2$-arom), 1.41 (t, J=6H, 2× CH$_3$ ethyl), 1.23–1.20 (m, 12H, CH$_3$, I—Pr); $^{31}$P-NMR (CDCl$_3$): δ=149.94; $^{13}$C-NMR (CDCl$_3$): δ=165.8 (C=O), 140.2 (C—CH2—O—P), 132.1 (2× C arom.), 131.1 (2× C—H arom), 129.7 (C H arom), 117.6 (CN), 64.7 (P—O—CH$_2$-arom), 61.4 (2× CH2 ethyl), 58.6 (O—CH$_2$—CH$_2$—CN), 43.4 (2× C—H I—Pr), 24.7 (4× CH$_3$ I—Pr), 20.5 (O—CH$_2$—CH$_2$—CN), 14.4 (CH$_3$ ethyl); HRMS 453.2156 ([M+H]$^+$ C$_{22}$H$_{34}$N$_2$O$_6$P requires 453.21545).

Experiment 1.5

Synthesis of Dimethyl 3,3'-(2-{[(2-cyanoethoxy) (diisopropylamino)phosphanyloxy]methyl}-2-{[2-(methoxycarbonyl ethoxy]methyl}propane-1,3-diyl-bisoxy dipropionate (compound 1d FIG. 8B)

To a solution of 300 mg (0.760 mmol) Tris-2,2,2-{ [(methoxycarbonyl)ethoxy]methyl} ethanol (CAS 169744-28-9; (Coutts, S.; Jones, D. S.; Livingston, D. A.; Yu, L.: 1995, Chemically-defined non-polymeric valency platform molecules and conjugates thereof, European patent application EP 0642798A2) in 2 ml dry dichloromethane at RT are added two drops of a 0.4 M solution of 1H-Tetrazole in dry acetonitrile (standard activator solution from solid phase DNA synthesis) and 274 mg (0.91 mmol; 1.1 eq) 2-cyanoethyl N,N,N',N'-tetraisopropylphosphorodiamidite (Aldrich;

CAS 102691-36-1) and stirred at RT until TLC shows complete consumption of the starting material (3 h). The solvent is removed in vacuo and the residue is purified by silica gel chromatography. Elution with ethyl acetate/n-heptane (2:3) containing few drops triethylamine afforded 240 mg (53%) of 1d as colorless oil.

$C_{26}H_{47}N_2O_{11}P$ $^1$H-NMR (CDCl$_3$): 3.88–3.71 (m, 2H, C—H), 3.68 (s, 9H, CH$_3$ ester), 3.65 (t, J=6.45 6H, 3× CH$_2$—O), 3.62–3.47 (m, 4H, 2× CH$_2$), 3.36 (s, 6H, 3× C—CH$_2$—O), 2.63 (t, J=7.25 Hz, 2H, C—CH$_2$—O—P), 2.54 (t, J=6.45 Hz, 6H, —CH$_2$—COOR), 1.19–1.16 (m, 12H, CH$_3$ iPr); $^{31}$P-NMR (CDCl$_3$): δ=148.6; HRMS: 595.2999 ([M+H]$^+$ $C_{26}H_{48}N_2O_{11}P$ requires 595.29957)

Figure 17:
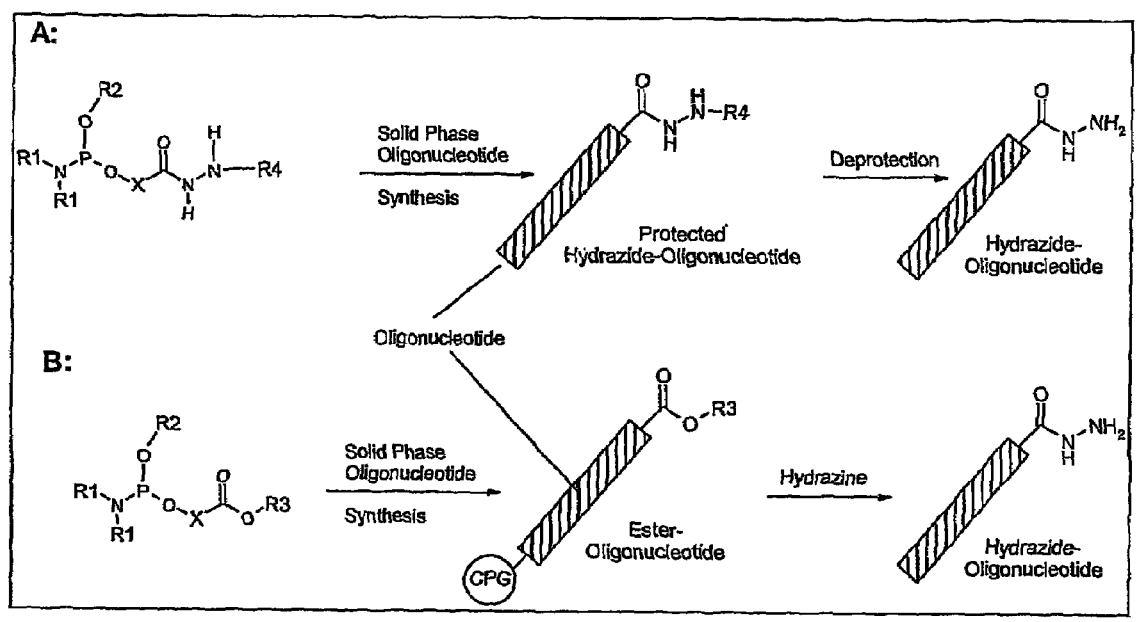
FIG. 17 shows the synthesis of a hydrazide modified oligonucleotide following two distinct protocols A and B. In A, a protected hydrazide phosphoramidite is used to modify the oligomer, which is then deprotected. In B, an ester phosphoramidite is used to modify the oligomer, which is then reacted with hydrazine.
Figure 18:
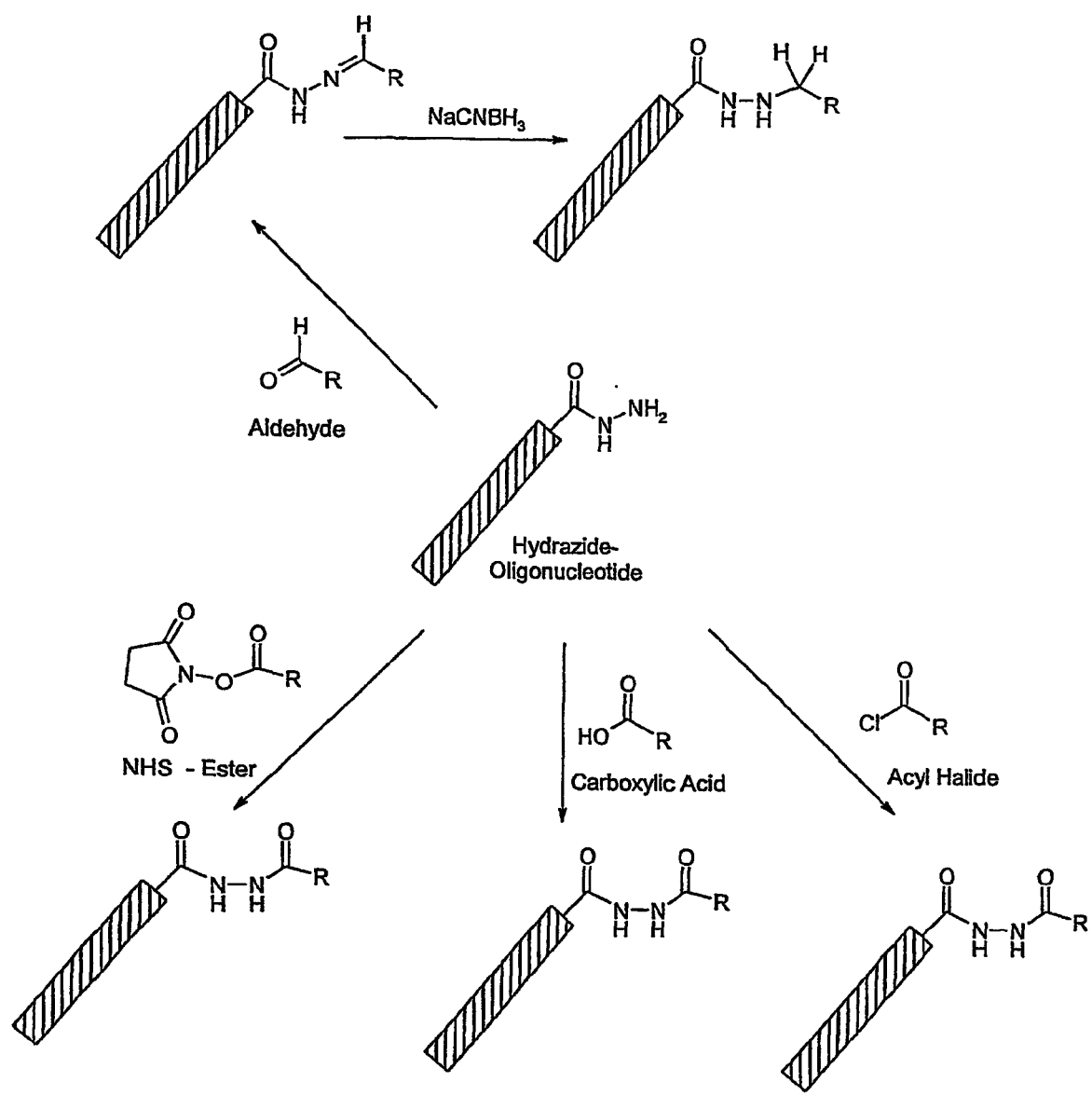
FIG. 18 shows a schematic illustrating the various functional groups which are capable of reacting with hydrazide modified oligomers.

Experiment 1.6 Synthesis of Oligonucleotides with Trityl Protected Hydrazide Amidites (e.g. Compound 1: See Also FIG. 17A):

Oligonucleotides are synthesized using solid phase phosphoramidite chemistry on an automated oligonucleotide synthesizer. The phosphoramidite with the protected hydrazide is applied as 0.1M solution in acetonitrile and coupled at the desired location in the sequence using standard activated reagents and coupling times.

The CPG bound oligo (1 mmol) is placed in a 1.5 ml test tube and treated with 2.0 ml conc. NH$_4$OH. After 2 h at 55° C. the ammonia solution is removed and evaporated to dryness under reduced pressure. The residue is dissolved in 1 ml water and filtered through a 0.45 μm syringe filter. The trityl protected hydrazide oligo is purified by reverse phase BPLC using a Merck LiChrospher RP 18, 10 μM, column (analytical: 4×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B. A gradient of 0% B to 100% B in 100 min is used for analytical and preparative separations. The fractions containing the trityl-on product were pooled and evaporated to dryness.

For the removal of the trityl protecting group the oligo is treated with 80% acetic acid for 30 min at RT. The acid is removed in vacuo, and the residue is dissolved in water then extracted twice with ethyl acetate. The aqueous layer is dried again and re-dissolved. Analytical HPLC usually shows a single product (is some cases as double peak) which can be employed for further reactions without purification. Alternatively HPLC purification can be performed using the solvent system described above.

Experiment 1.7 In Situ Generation of Hydrazide Functionality Synthesis of Oligonucleotides Using Phosphoramidites Containing Precursor Forms (e.g. Esters Such as Compound 1b FIG. 9B, Scheme 2: See Also FIG. 17B):

Oligonucleotides are synthesized using solid phase phosphoramidite chemistry on an automated oligonucleotide synthesizer. The phosphoramidite with the precursor form of the hydrazide is applied as 0.1 M solution in acetonitrile and coupled at the desired location in the sequence using standard activated reagents and coupling times. The use of a phosphoramidite that contains a hydroxyl group labeled with an acid-labile protecting group as well as a hydrazide precursor allows the introduction of the hydrazide at any position of the oligonucleotide because the precursor form of the hydrazide is stabile to the conditions of the oligonucleotide synthesis while the reactive hydrazide is not formed until incubation with hydrazine.

The CPG bound oligo (1 mmol) is treated with a solution of 50 mg diethylamine in 3.5 mL dichloromethane. After incubation overnight (light exclusion) the supernatant is removed and the support bound oligo is washed several times with dichloromethane and dried in vacuo.

For the cleavage of the benzoyl and isobutyryl protecting groups the conversion of the ester at the 5'-end of the oligo to a hydrazide, and the cleavage of the oligo from the support (FIG. 17B), the CPG with the bound oligo is treated with 1 ml 24% hydrazine hydrate. After 18 h under constant agitation at 4° C. the reaction is complete. The isolation of the oligo from the hydrazine solution can be achieved by reversed phase extraction (e.g. Sep-Pak or HPLC).

A C18 Sep-Pak cartridge (0.5 g Waters, No. 20515) is activated by rinsing with 10 mL acetonitrile and then 10 mL 0.1 M triethylammonium bicarbonate buffer pH 7.0 (TEAB). The hydrazine solution is diluted with the 5-fold volume of TEAB and applied to the cartridge. After binding of the oligo to the Sep-Pak column the residual hydrazine is washed away with 10 mL TEAB. The oligo is then eluted from the column with TEAB/acetonitrile (1:2). Oligo containing fractions are pooled and evaporated to dryness. For the RP-HPLC characterization and purification of the product the same conditions as described in protocol 1 can be applied.

Other examples are provided below wherein oligomers are processed to become linked to the multiple attachment moieties of the invention. The oligos are numbered in sequence of their respective description in this disclosure.

EXAMPLE 2

Experiment 2.1 Synthesis of Nonbranched Oligonucleotides 2.1.1 Oligo 9: Hydrazide-15mer: (1-TTT TTT TTT TTT TTT-3') SEQ ID NO. 1

The synthesis and deprotection was performed as described with amidite compound 1a. The trityl ON product elutes at 42.2 min under the conditions described. Oligo 9 elutes at 25.6 min (double peak). LRMS (ESI): M calc.: 4709.15, obs.: 4709.5.

2.1.2 Oligo 10: Hydrazide 19mer: (1-dGA TGA GCA GTT CTA CGT GG-3') SEQ ID NO. 2

The synthesis and deprotection was performed as described with amidite compound 1a. The trityl ON product elutes at 41.5 min under the conditions described. Oligo 10 elutes at 25.1 min (single peak). HRMS (ESI): M calc.: 6092, obs.: 6092.

2.1.3 In Situ Generation of Hydrazides (Oligo 11; Hydrazide 19mer (8-dGA TGA GCA GTT CTA CGT GG-Cy3) SEQ ID NO. 3

The synthesis of the oligonucleotide was performed as described previously. A CPG support loaded with Cy3 dye was used to label the fluorophor at the 3' end of the oligo. The CPG bound oligo was treated as outlined in Example 1 (E) above and the product was purified by RP-HPLC. The hydrazide oligo elutes at 31.8 min under the HPLC conditions described in Example 1 (D). LRMS (ESI): M calc.: 6599.7, obs.: 6598±2.

Experiment 2.2 Synthesis of Branching Oligonucleotides.

For the introduction of multiple hydrazides into oligonucleotides, branching phosphoramidites, phosphoramidites having more than one ester group which are converted into hydrazides, as well as a combination of both approaches were used. This flexible strategy allows the synthesis of oligonucleotides carrying defined numbers between one and up to several (~40) hydrazides. The experiments herein are described using p-RNA and are applicable to other oligonucleotides such as DNA.

Experiment 2.2.1 Synthesis of p-RNA Oligonucleotides

The synthesis of p-RNA oligonucleotides is performed as described in: Miculka, C.; Windhab, N.; Brandstetter, T. Burdinski, G; PCT patent application No. WO 99/15540 (1999) with the following exceptions and modifications: Phosphoramidites of pentopyranosyl nucleosides are dried in vacuo over KOH and dissolved in dry acetonitrile to give a 0.1 M solution. This solution is dried over freshly activated molecular sieve (3 Å) for 3 h and then applied for solid phase oligonucleotide synthesis on a PE Biosystems Expedite 8905 DNA synthesizer. Other phosphoramidites are dissolved at 0.1 M in dry acetonitrile and used without further treatment. For p-RNA oligonucleotides carrying a Cy3 dye at the 2'-end a CPG support custom loaded with monomethoxytrityl protected Cy3 (CAS: 182873-80-9, AP-Biotech, Freiburg, Germany) a 0.1 M solution of anhydrous pyridinium hydrochloride in dry acetonitrile is used as activator. The detritylation time for pentopyranosyl nucleosides is increased to 10 minutes and the coupling time is increased to 25 minutes. All other reagents and solutions and procedures are according to the recommendation of the instrument manufacturer.

Experiment 2.2.2 Deprotection of p-RNA Oligonucleotides:

For the cleavage of the β-cyanoethyl protecting groups the oligonucleotide is treated with a 1.5% (w/v) solution of diethylamine in dichloromethane overnight at RT (light exclusion). The supernatant is removed and the support bound oligonucleotide is washed several times with dichloromethane and dried in vacuo.

For the cleavage of the benzoyl and isobutyryl protecting groups, the conversion of the esters at the 5'-end of the oligo to hydrazides, and the cleavage of the oligo from the support, the CPG with the bound oligo is treated with 1 ml 24% hydrazine hydrate. After 18 h under constant agitation at 4° C. the reaction is complete. The isolation of the oligo from the hydrazine solution can be achieved by reversed phase extraction (e.g. Sep-Pak or HPLC).

A C18 Sep-Pak cartridge (0.5 g Waters, No. 20515) is activated by rinsing with 10 mL acetonitrile and then 10 mL 0.1 M triethylammonium bicarbonate buffer pH 7.0 (TEAB). The hydrazine solution is diluted with the 5-fold volume of TEAB and applied to the cartridge. After binding of the oligo to the Sep-Pak column the residual hydrazine is washed away with 10 mL TEAB. The oligo is then eluted from the column with TEAB/acetonitrile (1:2). Oligo containing fractions are pooled and evaporated to dryness. The characterization and purification of the products is achieved by reverse phase HPLC using a Merck LiChrospher RP 18, 10 μM, column (analytical: 4×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B. A gradient of 0% B to 100% B in 100 min (HPLC method A) or 30 min (HPLC method B) is used for analytical and preparative separations.

A. Oligo 12: Cy3 Labeled p-RNA Oligo with 1 Hydrazide: p-RNA Oligo 4'-(Hyd$_1$) TAG GCA TT (Cy3)-2'

The synthesis and deprotection was performed as described with amidite compound 1b.

B. Oligo 13: Cy3 Labeled p-RNA Oligo with 3 Hydrazides: p-RNA Oligo 4'-(Hyd$_3$) TAG GCA TT (Cy3)-2'

The synthesis and deprotection was performed as described with amidite compound 1d. The product elutes at 37.9 min (HPLC method A) under the conditions described. LRMS (ESI): M calc.: 3516.6, obs.: 3515.

C. Oligo 14: Cy3 Labeled p-RNA Oligo with 4 Hydrazides: p-RNA Oligo 4'-(Hyd$_2$)$_2$ (SBA) TAG GCA TT (Cy3)-2'

The synthesis and deprotection was performed as described with amidite compound 1c and with symmetric branching phosphoramidite (SBA; Clontech, No. 5252-2). The product elutes at 37.3 min (HPLC method A) under the conditions described. LRMS (MALDI): M calc.: 3784.7, obs.: 3784

D. Oligo 15: Cy3 Labeled p-RNA Oligo with 8 Hydrazides: p-RNA Oligo 4'-(Hyd$_2$)$_4$ (SBA)$_2$ (SBA) TAG GCA TT (Cy3)-2'

The synthesis and deprotection was performed as described with amidite compound 1c and with symmetric branching phosphoramidite (SBA; Clontech, No. 5252-2). The product elutes at 36.9 min (HPLC method A) under the conditions described. LRMS (MALDI): M calc.: 4661.1, obs.: 4464

E. Oligo 16: Cy3 Labeled p-RNA Oligo with Spacer and 8 Hydrazides: p-RNA Oligo 4'-(Hyd$_2$)$_4$ (SBA)$_2$ (SBA) (S18) TAG GCA TT (Cy3-2'

The synthesis and deprotection was performed as described with amidite compound 1c and with symmetric branching phosphoramidite (SBA; Clontech, No. 5252-2) and Spacer 18 (S18, Glen research No. 10-1918-02). The product elutes at 38.7 min (HPLC method A) under the conditions described.

F. Oligo 17: Cy3 Labeled p-RNA Oligo with 16 Hydrazides: p-RNA Oligo 4'-(Hyd$_2$)$_8$ (SBA)$_4$ (SBA)$_2$ (SBA) TAG GCA TT (Cy3-2'

The synthesis and deprotection was performed as described with amidite compound 1c and with symmetric branching phosphoramidite (SBA; Clontech, No. 5252-2). The product elutes at 38.7 min (HPLC method A) under the conditions described.

G. Oligo 18: p-RNA Oligo with 4 Hydrazides (without Cy3 Dye): p-RNA Oligo 4'-(Hyd$_2$)$_2$ (SBA) TAG GCA TT-2'

The synthesis and deprotection was performed as described with amidite compound 1c. The product elutes at 12.75 min (HPLC method B) under the conditions described. LRMS (ESI): M calc.: 3275.1, obs.: 3275.4.

Experiment 2.3 General Procedure for the Conversion of Hydrazide Oligonucleotides into Boronate Oligonucleotides 50 nmol hydrazide oligonucleotide are dissolved in 200 μL 10 mM ammonium acetate buffer pH 4.0 and 15 equivalents of 4-Formylphenlyboronic acid (Aldrich No. C43,196-6; CAS: 87199-17-5) per hydrazide are added. For an oligonucleotide containing 4 hydrazides for example 30 μL of a 0.1 M solution of 4-Formylphenlyboronic acid in DMSO (3 μmol) are used. The mixture is incubated at RT for 1 h, 20 equivalents NaCNBH$_3$ per 4-Formylphenlyboronic acid are added and incubation is continued for one other hour at RT. For example for the oligonucleotide with 4 hydrazides 150 μL (150 μmol) of a 1 M solution of NaCNBH$_3$ in 10 mM ammonium acetate buffer pH 4.0 (6.3 mg dissolved in 1 mL) are necessary.

The removal of excess 4-Formylphenlyboronic acid and Sodium Cyanoborohydride are removed by means of HPLC, gel filtration (Pharmacia PD 10 columns), or solid phase extraction (Merck LiChrolute columns). For boronate modified oligonucleotides it is crucial to use an endcapped BPLC column. Typical conditions are 5 μm Phenomenex Luna Phenyl Hexyl columns (analytical: 4.6×250 mm, flow=1.0 ml/min; preparative: 10×250, flow=3.0 mL/min) using 0.1 M triethylammonium acetate pH=7.0 (TEAA) as buffer A and 75% acetonitrile in buffer A as buffer B. A gradient of 0% B to 100% B in 100 min (HPLC method A) or 30 min (HPLC method B) is used for analytical and preparative separations. Product containing fractions are pooled and evaporated to dryness.

A. Olio 19: p-RNA Oligo with 1 Boronate: p-RNA Olio 4'-(PBA) TAG GCA TT (Cy3)-2'

The synthesis and deprotection was performed as described in the general protocol using oligonucleotide 12 as starting material.

B. Oligo 20: p-RNA Oligo with 3 Boronates: p-RNA Oligo 4'-(PBA)$_3$ TAG GCA TT (Cy3)-2'

The synthesis and deprotection was performed as described in the general protocol using oligonucleotide 13 as starting material.

C. Oligo 21: p-RNA Oligo with 4 Boronates: p-RNA Oligo 4'-(PBA)$_4$ (SBA) TAG GCA TT (Cy3)-2'

The synthesis and deprotection was performed as described in the general protocol using oligonucleotide 14 as starting material.

D. Oligo 22: p-RNA Oligo with 8 Boronates: p-RNA Olio 4'-(PBA)$_4$ (SBA)$_2$ (SBA) TAG GCA TT (C3)-2'

The synthesis and deprotection was performed as described in the general protocol using oligonucleotide 15 as starting material. The product elutes at 46.3 min (HPLC method A) under the conditions described.

E. Oligo 23: p-RNA Oligo with Spacer 18 and 8 Boronates: p-RNA Oligo 4'-(PBA)$_8$ (SBA)$_2$, (SBA) TAG GCA TT (CY3)-2'

The synthesis and deprotection was performed as described in the general protocol using oligonucleotide 16 as starting material.

F. Oligo 24: p-RNA Oligo with 16 Boronates: p-RNA Oligo 4'-(PBA)$_{16}$ (SBA)$_4$ (SBA)$_2$ (SBA) TAG GCA TT (C3)-2'

The synthesis and deprotection was performed as described in the general protocol using oligonucleotide 17 as starting material. The product elutes at 49.0 min (HPLC method A) under the conditions described.

G. Oligo 25: p-RNA Oligo with 1 Boronate: p-RNA Oligo 4'(PBA)-TAG GCA TT (Cy3)-2'

The synthesis and deprotection was performed as described in the general protocol using oligonucleotide 18 as starting material.

EXAMPLE 3

HPLC Analysis

Upon completion of the synthesis of hydrazide oligos, the first set of experiments examined the solution reaction kinetics of a hydrazide labeled oligo with an NHS or Sulfo-NHS ester. To a solution of 5 uL of 132 uM hydrazide ATA5 in 30 uL of 50 mM histidine was added 5 uL of 10 mM NHS acrylate. The solution was stirred at RT for a short period of time then injected into an HPLC system. The HPLC trace of the compounds in the solution indicated the quantities of hydrazide ATA5 and N'acrylo-ATA5 dihydrazide present in the reaction mixture for a given reaction time. The retention times of the starting ATA5 hydrazide and the modified ATA5 hydrazide were distinct and separable.

Figure 10:
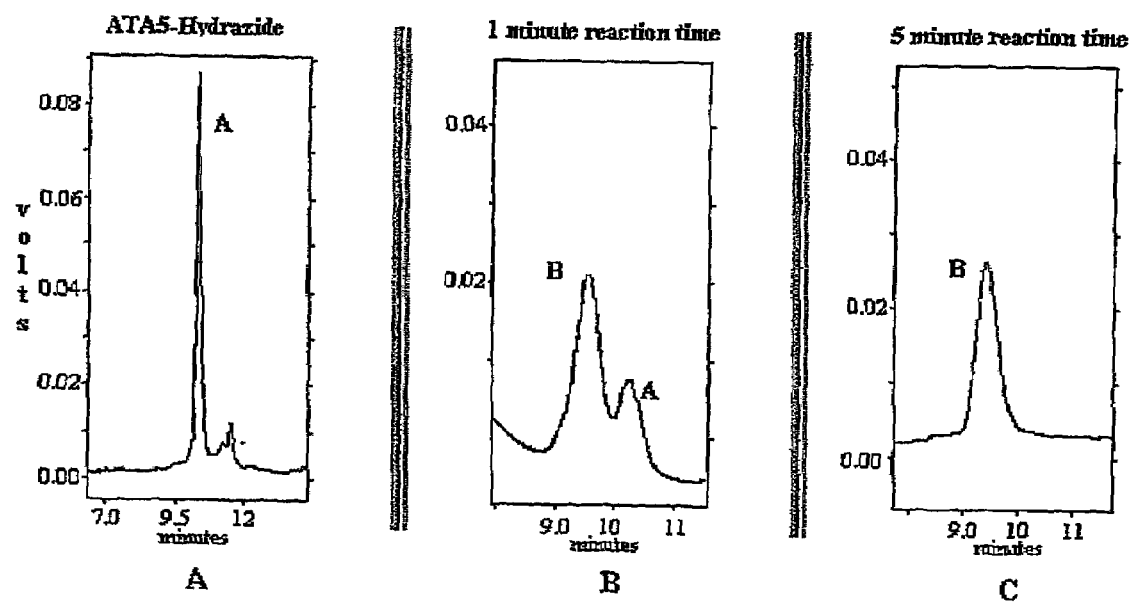
FIGS. 10A–C are graphs of three separate HPLC traces of the reaction mixture for coupling hydrazide-labeled oligo to an activated ester monomer such as that shown in Scheme 3 of FIG. 9.

FIGS. 10A–C show three separate traces of the reaction mixture. The first trace (A) was obtained from an unmodified ATA5 hydrazide (A), and the third trace (C) represents a completely modified ATA5 hydrazide (B) after a reaction time of 5 minutes with NHS acrylate. The middle trace (B) represents an incomplete modification captured 1 minute into the reaction. Given the approximate consumption of ATA5 hydrazide, a pseudo-first order reaction rate of 1200 $M^{-1}s^{-1}$ is determined.

Figure 11:
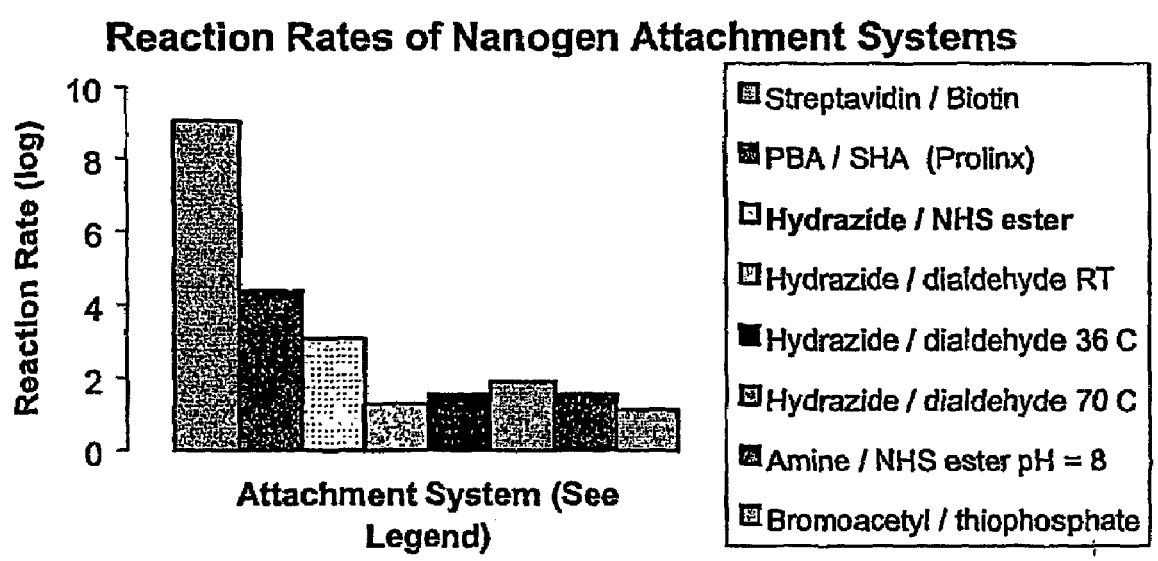
FIG. 11 is a graph that shows reaction rates for attachment of multi-labeled biomolecules. The hydrazide/N-hydroxysuccinimidyl (NHS) ester binding occurred at a rate measurably above that of other covalent binding systems and near to that of two noncovalent systems.

Comparison of this rate to other attachment systems utilized is shown in FIG. 11. The reaction rate for an NHS ester with a hydrazide in an aqueous environment represents an exceptionally efficient reaction. Furthermore, the pH of the reaction was altered to determine the pH dependence of the hydrazide modification. Experiments were carried out with a buffering system of 50 mM histidine adjusted with HCl to pH=6, 5.5, 5.0, 4.5, and 4. The transformation continued down to pH=4.5. However, at pH=4, the hydrazide oligo was unaffected, constituting no transformation and therefore a pH lower limit of approximately 4.5.

EXAMPLE 4

Chip Preparation

Microarray containing chips are plasma cleaned 5 minutes under Argon. The 25 site 1 cm by 1 cm chips are then silanized using vapor phase deposition. To the center of the microarray is added 0.10 uL of a 20% (by mass) solution of 9:1 (molar ratio) acrylamide/bisacrylamide in 1:1 DMSO/H$_2$O with 0.3% Daracur 4265 as a UV initiator. The chip is placed into a microreaction molding system to which the microarray site is pressed to a UV window containing a square 4 uM cavity, 3.mm on a side. The solution is irradiated for 20 sec with UV light, removed from the molding system, rinsed with water and air dried. The well forms a square hydrogel layer over the microarray. Excess polymerization, beyond the parameters of the mold, is removed.

To the existing permeation layer is added 0.80 uL of a solution containing 20% (by mass) monomer concentration of NHS or Sulfo-NHS/Am/Bis 10/83/7 (molar ratio) and allowed to saturate the existing polymer for 1 minute. The chip is loaded onto the microreaction molding system and polymerized as above with a circular mold with a diameter of 4.6 mm and a well depth of 5 uM. This second mold completely encompasses and extends beyond the existing square layer. Attachment of the second layer is accomplished through intercalation of polymer chains and bind silane. The chips are washed with water and dried with compressed air and subsequently tested in the following experiments.

Experiment 4.1: Activated Ester Concentration: Labeled Capture Address.

To chips modified with the two fold permeation layer as described above containing 0, 1, 2 and 4% Sulfo-NHS was electronically loaded 500 hydrazide-T12-BTR as a specific labeled capture while 50 mM nM biotin-T12-BTR was used as a nonspecific labeled capture. All solutions were buffered in 50 mM histidine. Captures were addressed at a current of 500 nA/pad for 120 seconds, 4 pads at a time. Each chip was washed with 1% SDS, 0.2× STE and soaked in 1% SDS for 20 minutes. The chips were imaged for 1 second and the average MFI values were recorded.

Figure 12:
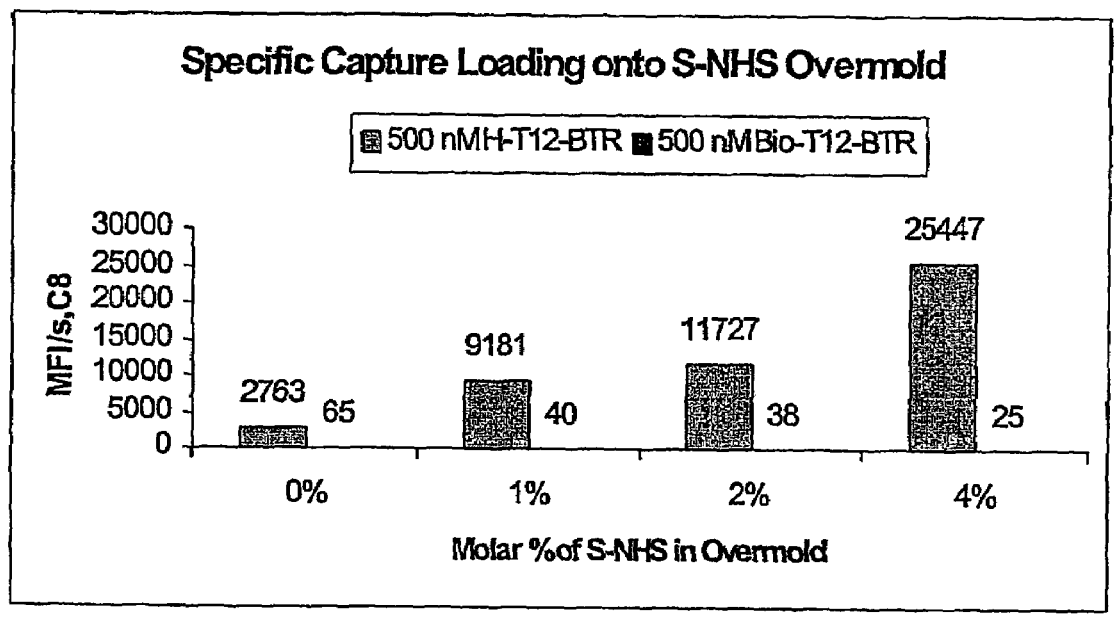
FIG. 12 is a graph that shows that covalent attachment of the labeled hydrazide oligo is dependent on the amount of activated ester in the substrate surface.

As can be seen by in FIG. 12, the covalent attachment of the labeled hydrazide oligo is dependent on the amount of activated ester in the permeation layer and increases as the concentration increases. The nonspecific attachment of a biotin labeled oligo is also quite low, averaging 40 MFI/s for the experiment.

Experiment 4.2: Electronic Conditions:

To chips modified with the two fold permeation layer as described above containing 10% NHS or Sulfo-NHS was electronically loaded 500 and 5 nM hydrazide-T12-BTR as a specific labeled capture. 500 mM nM biotin-T12-BTR was used as a nonspecific labeled capture. All solutions were buffered in 50 mM histidine. Captures were addressed at currents of 400, 500, 600, 700 and 800 nA/pad for 120 seconds, 3 pads at a time. Nonspecific captures were loaded at 800 nA/pad. Each chip was washed with 1% SDS, 0.2× STE and soaked in 1% SDS for 20 minutes. The chips were imaged for 1 second and the average MFI values were recorded.

Figure 13:
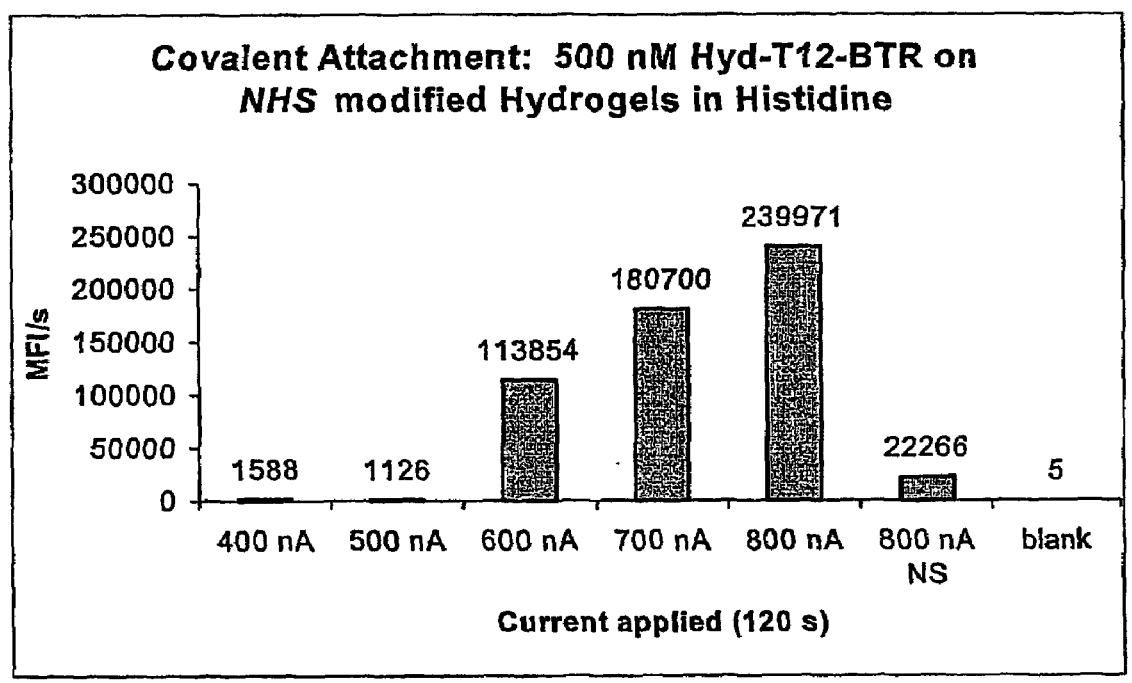
FIGS. 13 and 14 are graphs showing the proficiency of covalent attachment for either NHS or N-hydroxy-sulfosuccinimidyl (Sulfo-NHS) ester modified substrate surfaces respectively. The graphs show the specific and nonspecific fluorescent intensity from labeled oligomers attached to the electrodes over a range of applied currents.
Figure 14:
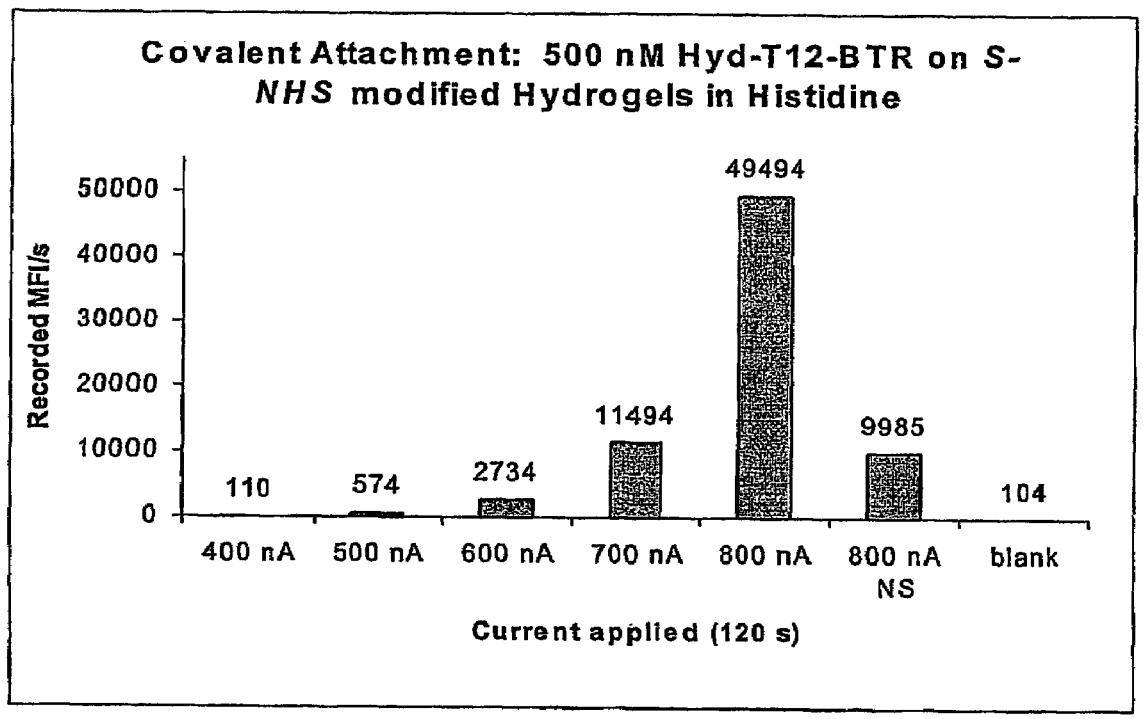

As can be seen by in FIG. 13, attachment of a specific capture to the NHS modified permeation layer dramatically increases at 600 nA, while Sulfo-NHS modified hydrogels required a slightly higher current for maximum attachment (FIG. 14).

Experiment 4.3: Effect of Multiple Binding

To chips modified with the two fold permeation layer as described above containing 10% NHS were loaded Cy3 labeled ATA5 oligos containing 1, 2, 4, or 8 hydrazide moieties. The four oligomers were electronically addressed at 500 nM with a current of either 700 or 800 nA/pad for 120 s, buffered in 50 mM histidine. Upon completion, the chips were washed and the binding levels were measured.

Figure 15:
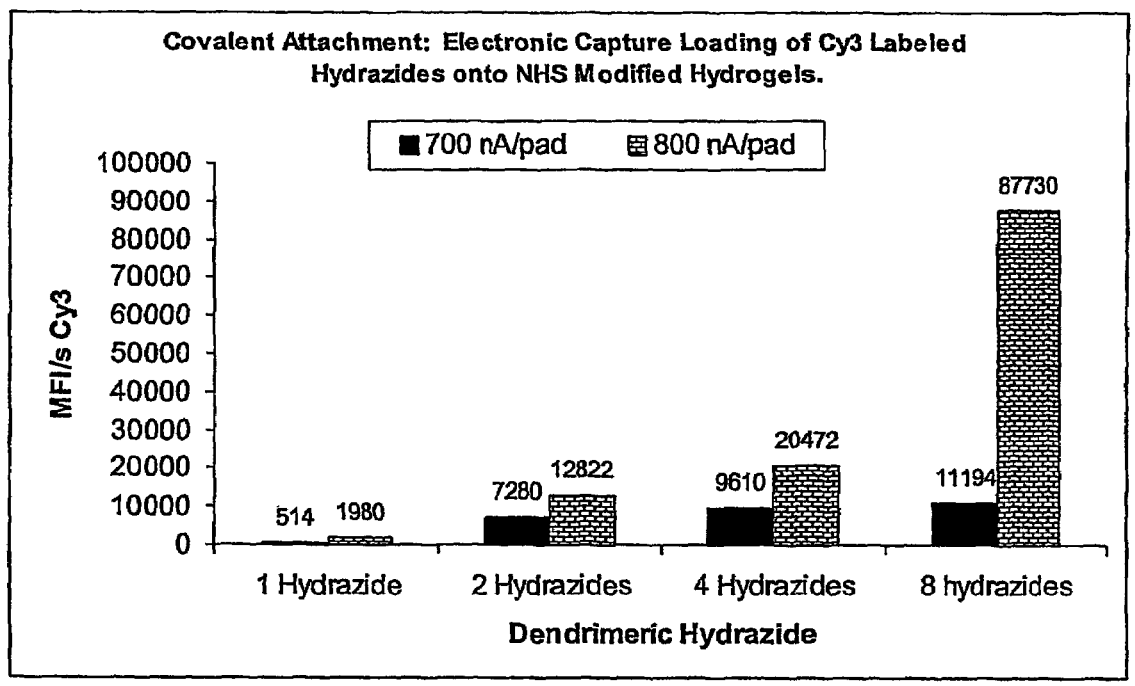
FIG. 15 is a graph that shows that multiple binding of hydrazide moieties provides higher level of detection of the biomolecule on the substrate.

The recorded MFI/s values are displayed in FIG. 15. A comparison the number of hydrazide moieties available for attachment per oligomer given equal currents indicates an increased binding level with the increase in hydrazides to the oligomer.

Experiment 4.4: Reverse Dot-Blot Electronic Hybridization

To chips modified with the two fold permeation layer as described above containing 15% NHS was loaded an octa-hydrazide ATA5 oligomer with a Cy3 label as a specific capture. The specific capture was loaded at 500 nM with a current of either 600 or 700 nA/pad for 120 s, buffered in 50 mM histidine. Electronic Hybridization was carried out with 5 nM RCA5-T12-Cy5 as a specific target while a solution of 5 nM RCA4Cy5 was used as a nonspecific target. The targets were loaded at 400 nA/pad for 60 seconds, the chips were washed according to the standard protocol and imaged.

Figure 16:
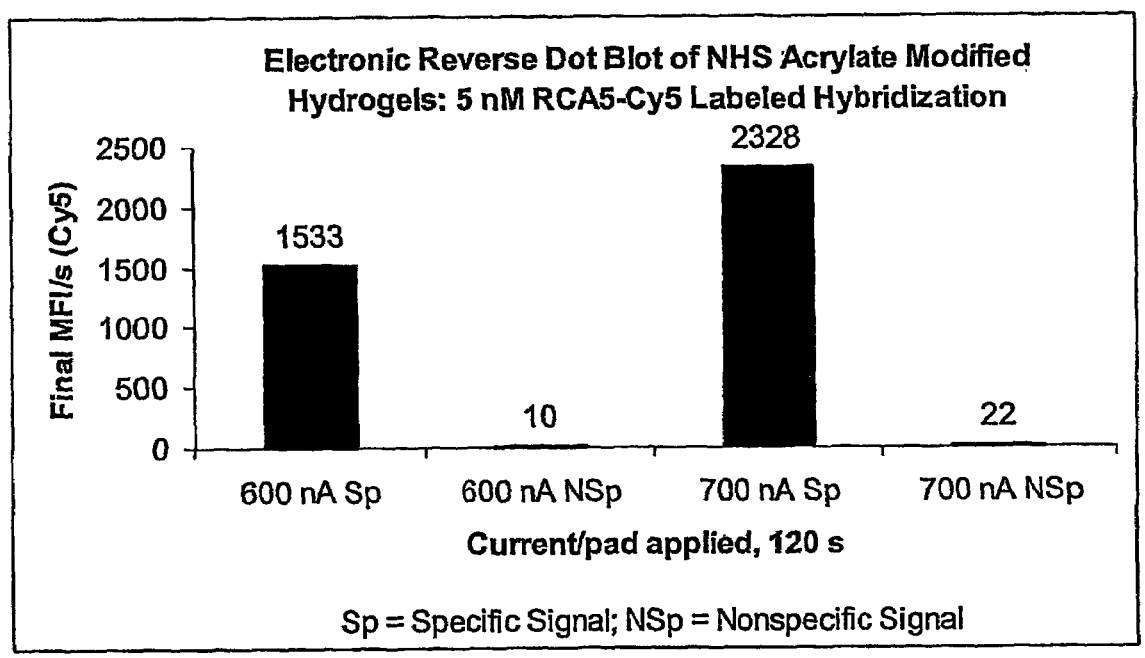
FIG. 16 is a graph that shows results of an electronic reverse dot blot in which hybridization was completed only on those sites containing a hydrazide-modified oligonucleotide (ATA5). The capture probes were specifically bound to an activated-ester-containing substrate under appropriate electronic conditions. The nonspecific captures without a hydrazide do not react with the activated ester and are therefore unavailable for hybridization.

The data presented in FIG. 16 clearly indicates the hybridization of the specific target preferentially to the nonspecific target. It should also be noted that in agreement with data reported above, the increase in current, from 600 to 700 nA for the electronic loading of the capture results in an increase in the hybridization.

EXAMPLE 5

Synthesis of Biomolecules Having Noncovalent Binding Moieties

Figure 4:
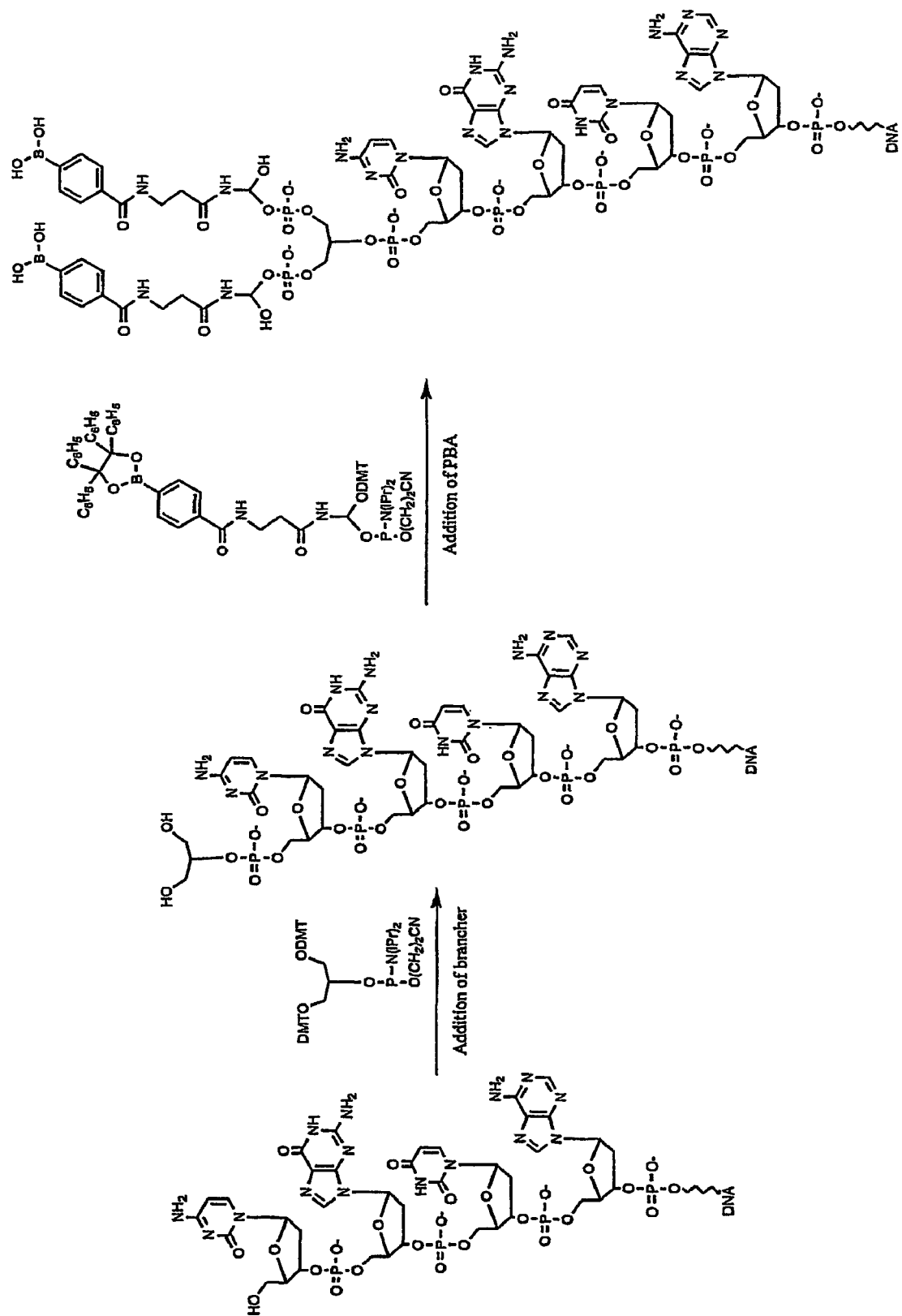
FIG. 4 shows a series of chemical steps to produce a structure having a dendrimeric structure containing phenyl boronic acid (PBA) attachment moieties.
Figure 5A:
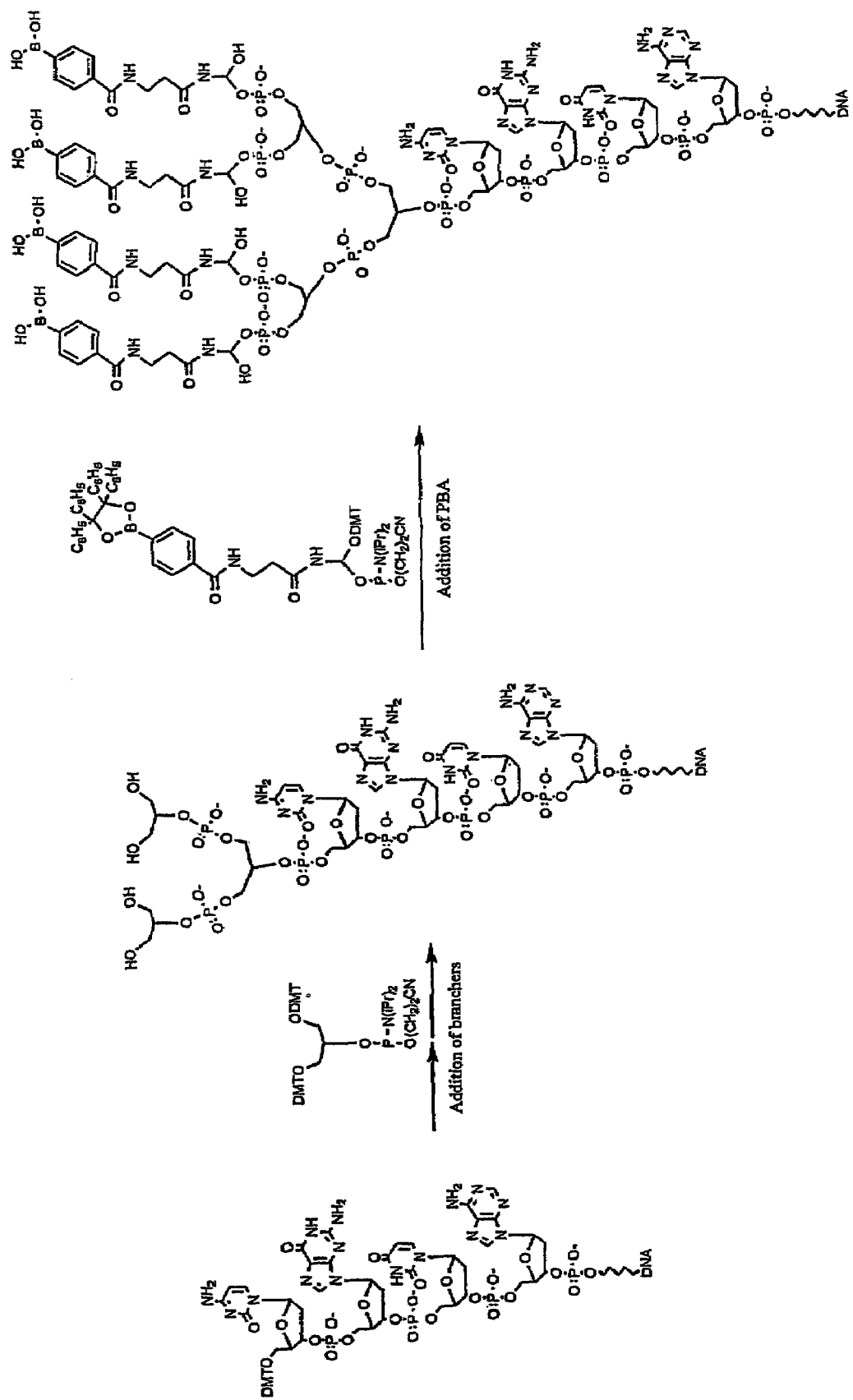
FIGS. 5A and B show a series of chemical steps to produce chemical structures comprising oligonucleotide biomolecules having either four (A) or eight (B) binding moieties for noncovalent binding of the biomolecule to a substrate surface.
Figure 5B:
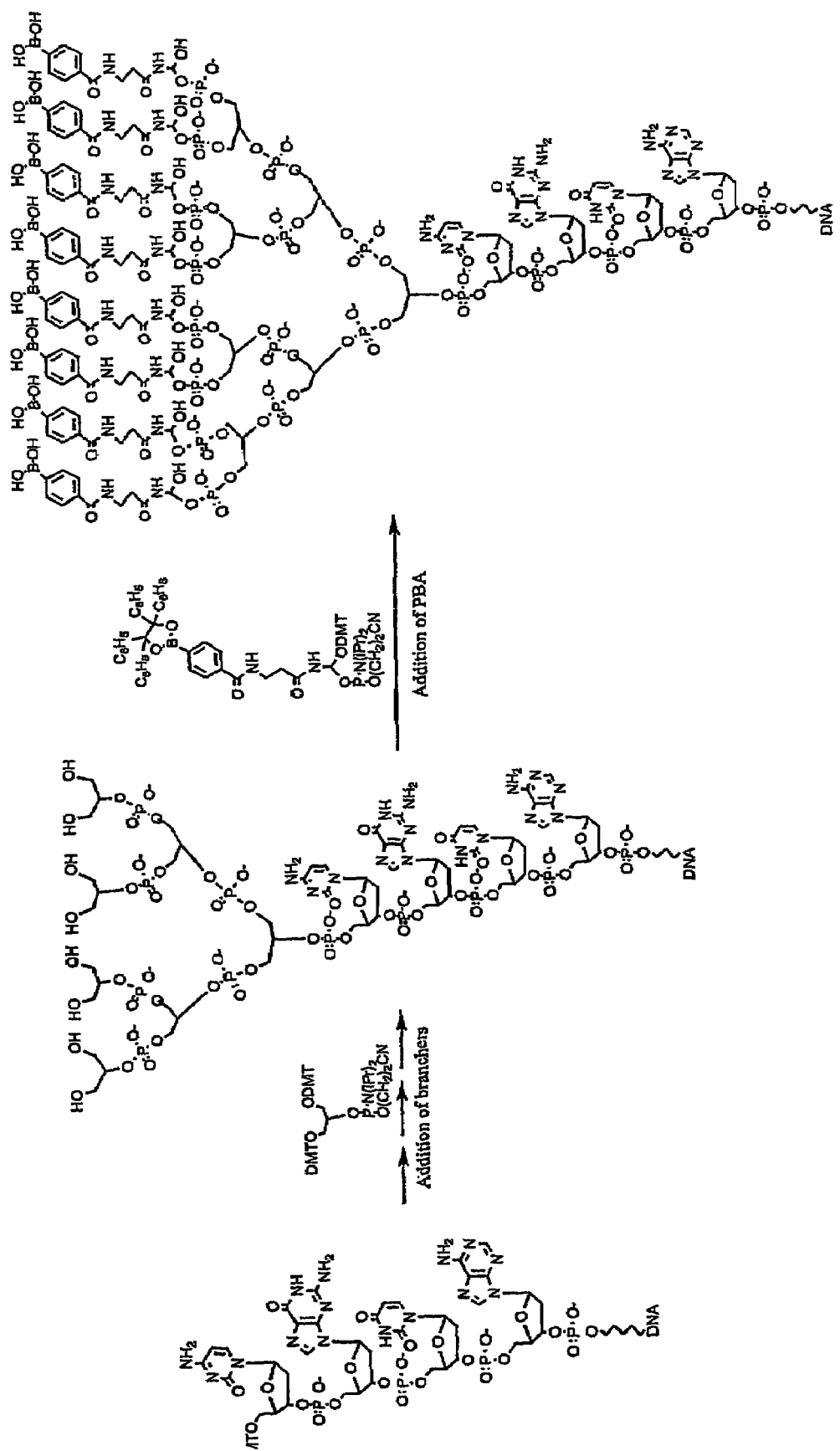

FIGS. 4 and 5A and B depict the syntheses of oligonucleotides containing multiple binding moieties. In FIG. 4, oligo synthesis is depicted wherein there is added a single branched phosphoramidite containing two PBAs. FIGS. 5 A and B show two branches with four PBAs, and three branches with eight PBAs, respectively. Syntheses as depicted were carried out on an ABI394 DNA Synthesizer. The stepwise coupling yield of branched phosphoramidite was similar to the regular nucleotide phosphoramidites, about 96–98%. The PBA phosphoramidite was applied at the last step. The cleaving of oligonucleotides from the solid support and the removal of protecting groups were the same as the handling of regular oligonucleotides as is well known to those of skill in the art.

The PBA-containing branched oligonucleotides were purified and analyzed by HPLC. The HPLC of PBA-containing oligonucleotide showed a broader peak than that of a regular oligonucleotide.

Experiment 5.1: Electronic Loading of Biomolecules Via Non-Covalent Binding Moieties.

20 nM non-branched and branched PBA-containing ATA5 capture probes were loaded on hydrogel substrates electronically. The capture probes were loaded in 50 mM histidine, 10 pads at a time for 120 seconds. 20 nM RCA5-BTR was loaded passively for 5 minutes. The substrates were washed and imaged. Analysis showed that both branched and unbranched capture probes were immobilized to the permeation layer, as desired.

Experiment 5.2: Stability of Electronically Loaded Biomolecules Via Non-Covalent Binding Moieties.

Figure 21:
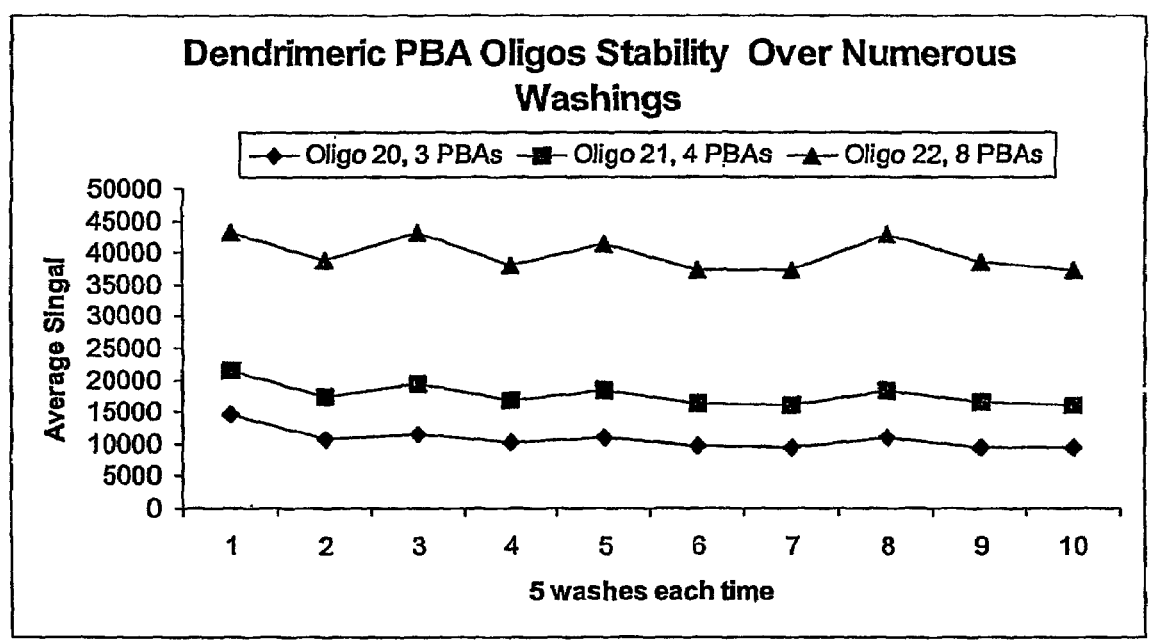
FIG. 21 shows the recorded mean fluorescent intensity (MFI) values for oligomers labeled with 3, 4, and 8 phenylboronic acids per oligo. The attached oligomers were subjected to vigorous washing conditions to monitor the stability of the attachment system.

Oligos 20, 21 and 22 (p-RNAs containing 3,4, and 8 PBA binding sites) were electronically addressed to SHA modified hydrogel chips. Upon completion, initial images were recorded after a standard washing procedure previously described. The chip arrays were then subject to regular irrigation with repeated rinsing with 10 uL of 50 mM histidine. Images were recorded after 5 washings. The results shown in FIG. 21 contain 2 features. Primarily the recorded signals for the higher order dendrimers which have a higher number of attachment sites per oligo is distinctly higher. Also, the signal is quite stable over a period of 25 wash cycles illustrating the improved stability of the use of dendrimeric attachment systems. Oligo 22 has lost approximately 14% of its initial signal while oligos 20 and 21 have decreased 25 and 35% respectively.

EXAMPLE 6

Covalent Attachment Via Multiple Hydrazone Formation

Figure 22:
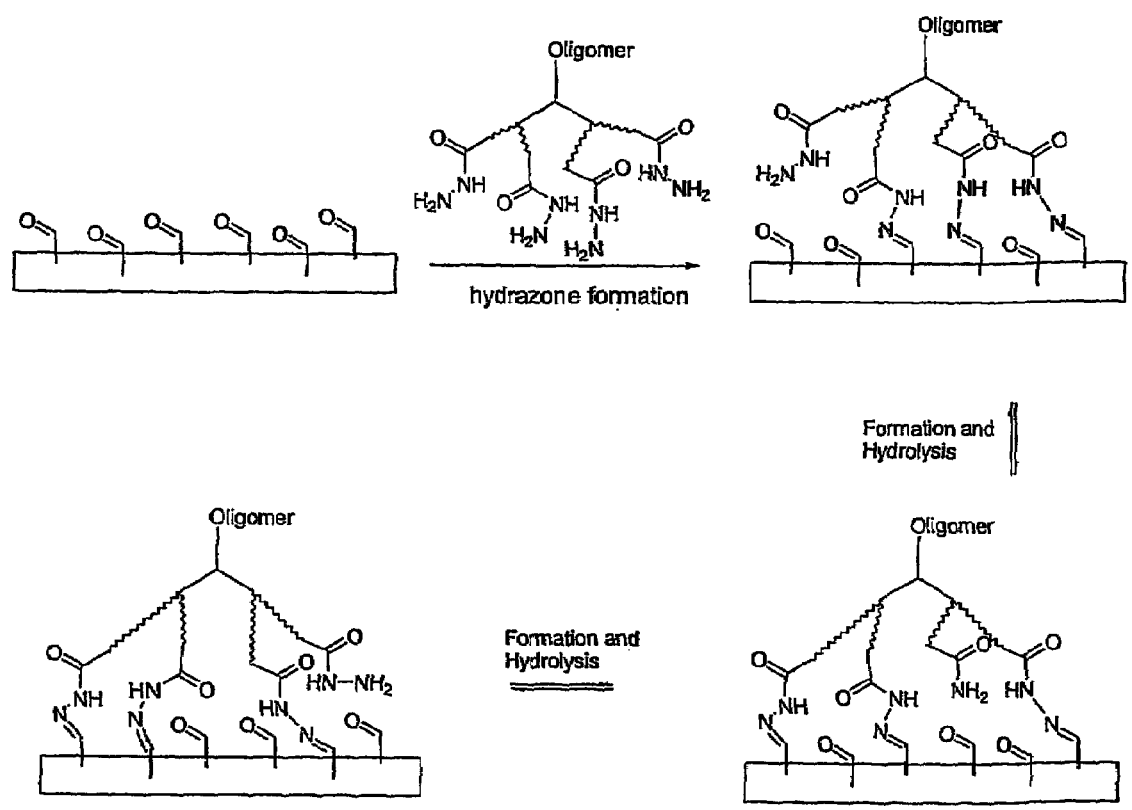
FIG. 22 shows a schematic illustrating the dynamic equilibrium and stability of dendrimeric hydrazides onto an aldehyde rich permeation layer. The oligomer, displayed with four hydrazide moieties, is electronically loaded onto an aldehyde rich permeation layer resulting in multiple hydrazone linkages. In this particular example, the linkages individually are susceptible to hydrolysis. The stability gained with the use of multiple attachment sites allows for hydrolysis of some hydrazones while others remain intact. The hydrazide, tethered through neighboring hydrazone attachment sites, is incapable of diffusion and is therefore retained within the aldehyde rich permeation layer capable of re-establishing the linkage.

Previously, oligos modified with a single amine or hydrazide have been electronically loaded onto aldehyde modified hydrogels. The interaction of an aldehyde with an amine or hydrazide results in the formation of an imine (carbon with a double bond to nitrogen) or a hydrazone respectively. These moieties are reversible under aqueous conditions and require further reduction with $NaBH_3CN$ to form a stable irreversible covalent attachment. Indeed, electronic concentration of an oligomer containing a single hydrazide resulted in attachment of the oligomer to the surface via hydrazone formation. Elimination of the reduction step resulted in a readily hydrolyzed and unstable linkage in which the bound oligo readily diffused away. The use of dendrimeric hydrazides provides a means of covalent attachment through a somewhat unstable linkage which does not require further reduction; provided there are a significant number of hydrazones formed per oligo. The reversible hydrazone formation can occur with some linkage sites while others remain intact (FIG. 22). The hydrazide is incapable of diffusion, and trapped within an aldehyde rich environment, can readily reform. This equilibrium takes advantage of the increased number of attachment sites per oligo and, provided all linkages do not hydrolyze at once, is contemplated to provide a stable attachment system. Aldehyde rich permeation layers can be prepared directly, as in glyoxyl agarose, or can be obtained from an acetal modified permeation layer. In the latter, the acetal moiety is readily hydrolyzed in the presence of acid to afford an aldehyde. The acetal serves as a protecting group, preserving the aldehyde functionality until activation is desired. Hydrolysis can be completed with exposure to an acidic solution for 1 hr or subjected to a mild electronic current buffered in a dilute salt solution. The latter method provides site specific hydrolysis by taking advantage of the acid generated at the cathode.

Experiment 6.1: Dendrimeric Hydrazide Oligomers Attached to Glyoxyl Agarose.

Figure 23:
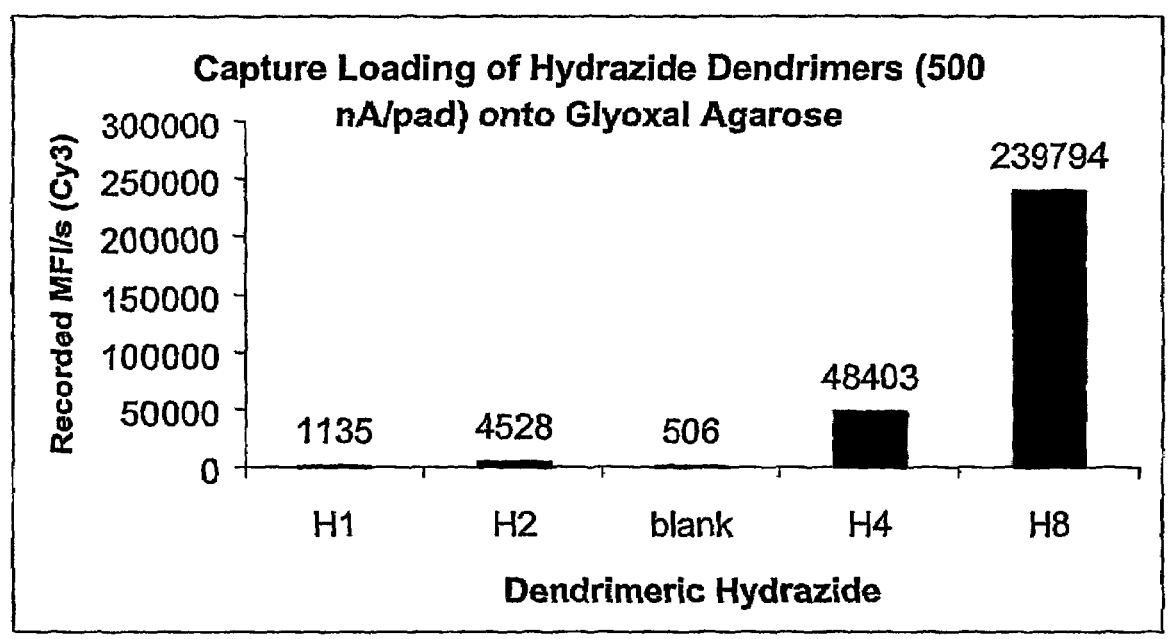
FIG. 23 is a graph showing the attachment of dendrimeric oligomers of 1, 2, 4, and 8 hydrazides onto glyoxyl agarose permeation layers coupled via hydrazone linkage(s).

Standard 25 site chips were spin coated with glyoxyl agarose (FMC, Princeton, N.J.)). 500 nM Hydrazide Cy3 labeled oligos containing 1, 2, 4, and 8 hydrazides were electronically loaded at 500 nA/pad for 2 minutes each, buffered in 50 mM histidine. The chips were washed according to established procedure and imaged. The recorded MFI/s values are displayed in FIG. 23. The oligos with one or two hydrazides were quite unstable and as expected afforded little or no detectable fluorescence beyond the background noise. The oligos with a higher number of hydrazides are capable of forming a stable covalent attachment.

Experiment 6.2: Dendrimeric Hydrazide Oligomers Attached to Acetal Modified Hydrogels: Deprotection and Covalent Attachment.

Standard 25 array site microchips were modified with a single layer hydrogel composed of acrylamide, bisacrylamide and vinyl acetal in a 15:2:3 ratio. Selected sites were predisposed to a current of 300 nA/pad for 2 minutes in a 50 mM NaCl solution to hydrolyze the acetal functionality exposing the aldehydes. Dendrimeric hydrazide oligomers containing 8 hydrazides per oligo were electronically loaded at 500 nA/pad for 2 minutes buffered in 50 mM histidine to pads which had been activated and to those that had not. A nonspecific oligo was also electronically loaded onto both acetal and aldehyde modified sites. After a standard wash cycle, the chips were imaged. The recorded MFI/s data is displayed in FIG. 24.

Figure 24:
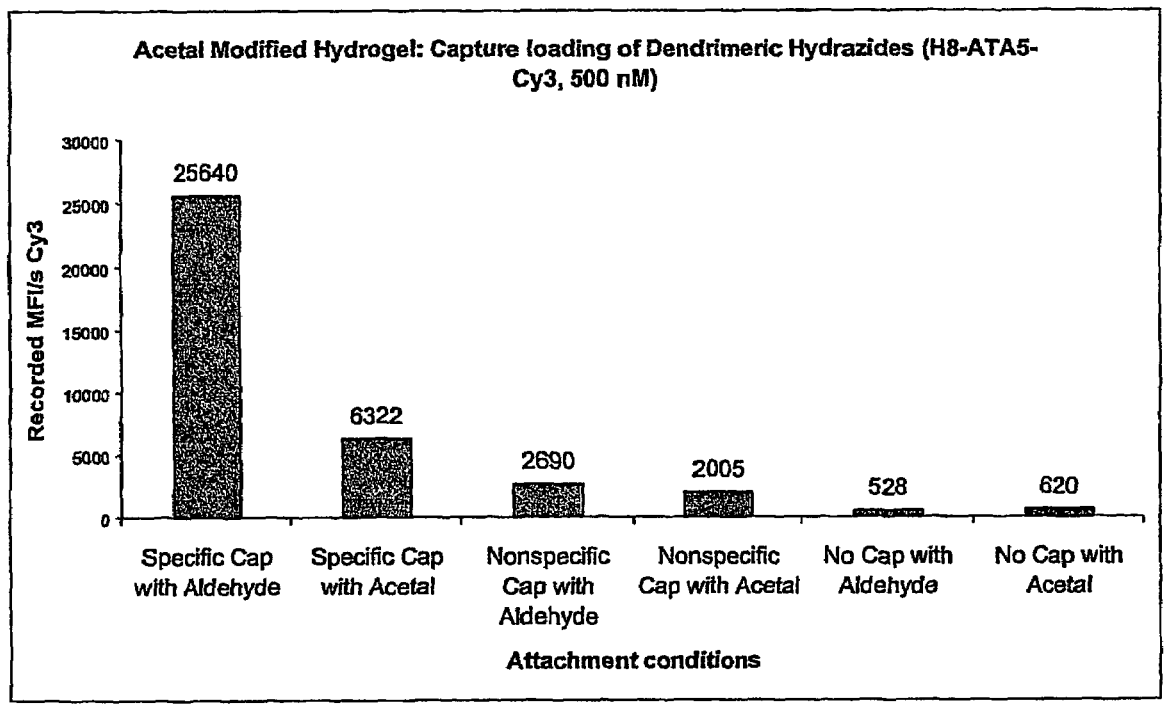
FIG. 24 is a graph showing the attachment of dendrimeric oligomers onto an acetal modified hydrogel. The acetal moieties require hydrolysis with acid to generate aldehydes for covalent attachment capabilities.

As can be seen in FIG. 24, pads which had been electronically activated, then loaded electronically with a dendrimeric labeled oligomer exhibit the highest fluorescence signal. Interestingly, those pads which were not pre-addressed, remaining as acetals also indicate some attachment of hydrazide modified oligomers. Presumably, the electronic current applied to concentrate the oligomer generated enough acid to surpass the buffering capacity of histidine locally and was therefore able to hydrolyze a significant quantity of acetal moieties.

EXAMPLE 7

Figure 19:
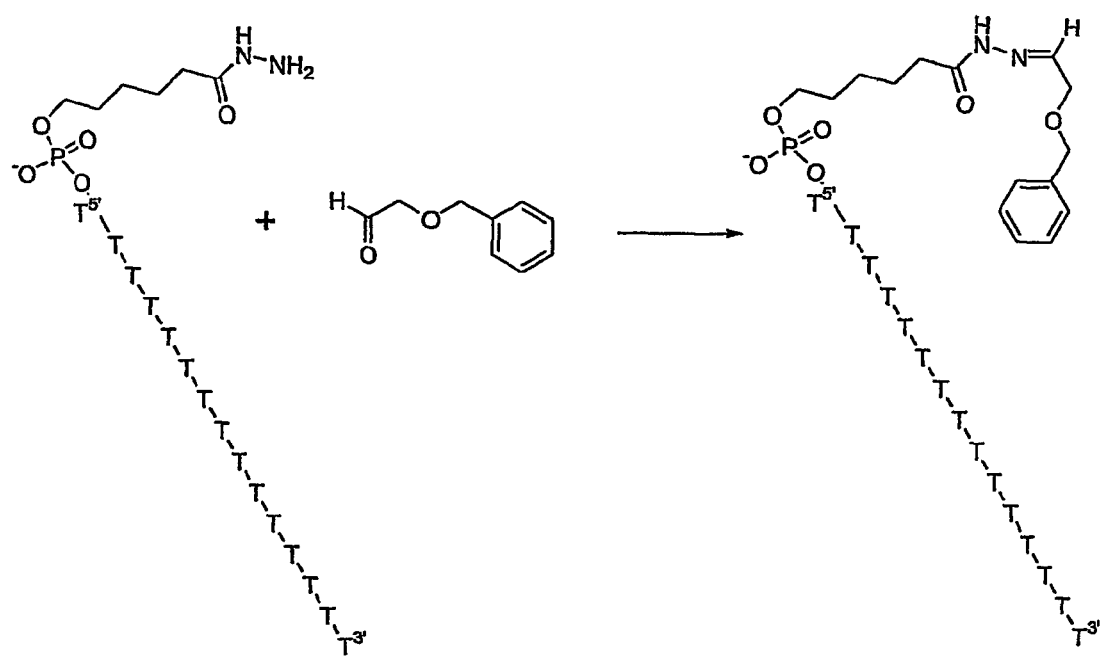
FIGS. 19 and 20 are examples of hydrazide oligomers condensing with aldehydes.

Coupling of Hydrazide Oligonucleotides to Molecules Other than Substrate Surfaces Experiment 7.1 Reaction of Hydrazide-15mer 9 with Benzyloxy Acetaldehyde: FIG. 19.

10 µmol Hydrazide Oligonucleotide 9 are dissolved in 60 µL 10 mM ammonium acetate buffer (pH 4.0). 1 drop benzyloxyacetaldehyde (CAS: 6065-87-3; C9H10O2 [150.1760] Aldrich No. 38,218-3) is added and the mixture is allowed to stand at RT for 1 h. The solvent and excess of aldehyde is removed in vacuo and the product is analyzed by HPLC (Column: Merck LiChrospher RP 18, 10 µM, 4×250 mm; Buffer A=0.1 M triethylammonium acetate pH=7.0, Buffer B=75% acetonitrile in buffer A; Flow=1.0 mL/min; Gradient: 0% B to 100% B in 100 min). The retention time of the product is 30,7 min, oligo 9 elutes at 25.5 min.

Figure 20:
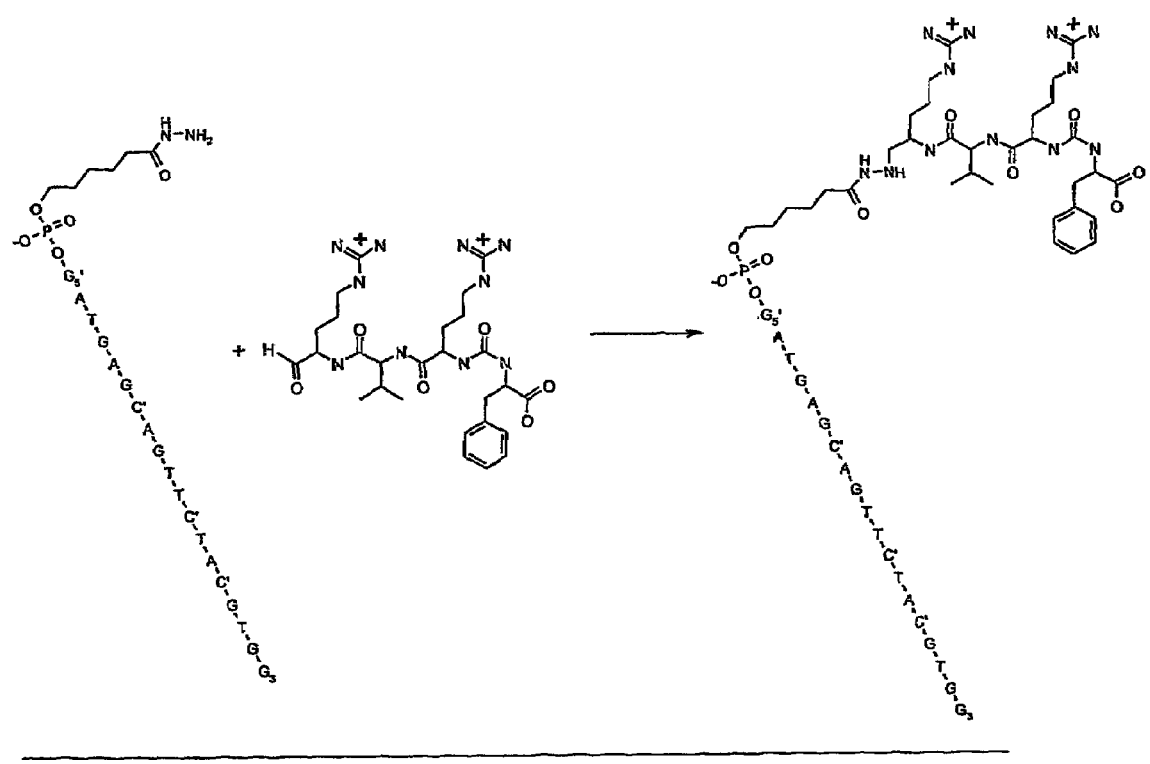

Experiment 7.2 Conjugation Reaction of Oligo 10 with a Peptide FIG. 20.

4.4 nmol Oligo 10 are dissolved in 60 µL 10 mM ammonium acetate buffer (pH 4.0). 44 nmol (10 eq.) antipain hydrochloride (CAS: 37682-72-7; C27H44N10O6.2 HCl; [677.6304]; Calbio No. F 178220) in 15 µL buffer are added and agitated 3 h at RT. The intermediate product is reduced with NaBH$_3$CN (100 eq.) for 1 h at RT. The product is isolated by HPLC (Column: Merck LiChrospher RP 18, 10 µM, 4×250 mm; Buffer A=0.1 M triethylammonium acetate pH=7.0, Buffer B=75% acetonitrile in buffer A; Flow=1.0 mL/min; Gradient: 10% B to 85% B in 60 min). The retention time of the product (oligonucleotide peptide conjugate) is 16.5 min, oligo 10 elutes at 13.9 min. MS (ESI): calc: 6680.6; obs.: 6679.6)

EXAMPLE 8

Passive Application of Hydrazide Modified Biomolecules on Slide Surfaces

For the binding of hydrazide modified oligonucleotides to commercially available slides a series of p-RNA oligonucleotides containing 1 to 16 hydrazides were used. Along with oligonucleotides 12, 13, and 14, oligomers with 3 and 6 hydrazides, prepared from 1d, were used. Additionally, an amine terminated oligomer (prepared with 5' Amino Modifier C6; Glenn Research) and an oligonucleotide without modification are used as nonspecific controls. All oligomers are labeled with Cy3 at the 2' end and retain the same nucleotide sequence.

Experiment 8.1: Attachment to Surmodics 3D Links Amine Binding Slides.

Figure 25:
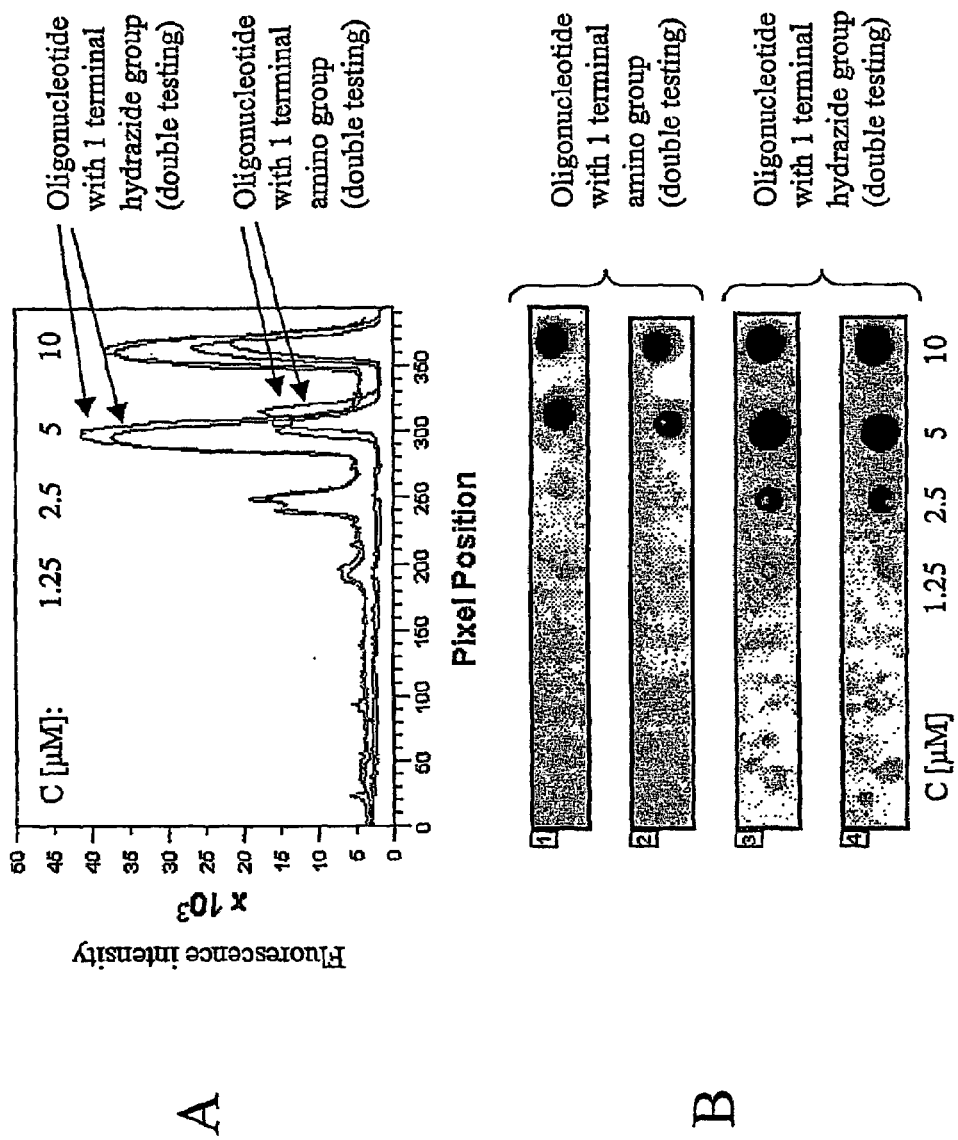
FIG. 25 illustrates the use and improved binding of hydrazide oligomers on Surmodics 3D Links Amine Binding Slides at various concentrations.

Oligonucleotides are dissolved in 3D Link™ print buffer (Surmodics, Inc, Eden Prairie, Minn.) at pH=8.5 with concentrations ranging between 10 µM and 100 nM. From each solution, 0.5 µL was applied directly to the slide surface and incubated at room temp. in a sealed chamber above a saturated NaCl solution overnight in the dark. The slides are then treated for 15 min at 50° C. with 3D Link™ blocking buffer to block unreacted surface sites. The slides were washed twice with water followed by a 30 min wash with 0.2% SDS at 50° C. and finally two water washings, then allowed to air dry. The fluorescence detection was preformed on a Pharmacis scanner with 20 second integration times. Images as well as intensity profiles are displayed in FIG. 25.

The nonspecific oligonucleotide afforded a signal between $10 \times 10^3$ and $25 \times 10^3$ relative units at 10 µM. The signal compares in intensity with that observed for an oligonucleotide containing a single amino group. In contrast, the hydrazide modified oligonucleotide affords a much higher loading of $35-40 \times 10^3$ fluorescence units. Further, the hydrazide modified oligonucleotide has a higher fluorescence signal at lower concentrations, with a lower limit of detection of 1.25 µM, as compared to the amine modified oligomer which has a lower detection limit of 5 µM.

Experiment 8.2: Attachment to SuperAldehyde Slides.

Oligonucleotides are dissolved in either Surmodics 3D Links print buffer at pH=8.5 with concentrations ranging from 10 µM to 100 nM or in 10 mM ammonium acetate buffer at pH=4.0. From each solution, 0.5 µM are applied to the surface of SuperAldehyde slides (Telechem International, Inc Sunnyvale, Calif.) and allowed to incubate overnight at rt. The slides are then treated twice with 0.2% SDS and washed 4 times with water (2 min each). The surface was then treated with a solution of 0.3% NaBH$_3$CN in PBS buffer, pH=7, with 133 mL ethanol to eliminate bubbling. This was followed by three 1 min washings with 0.2% SDS and water. Fluorescence detection was preformed on a Pharmacis scanner with 20 s integration times. Images as well as intensity profiles are displayed in FIG. 26.

Figure 26:
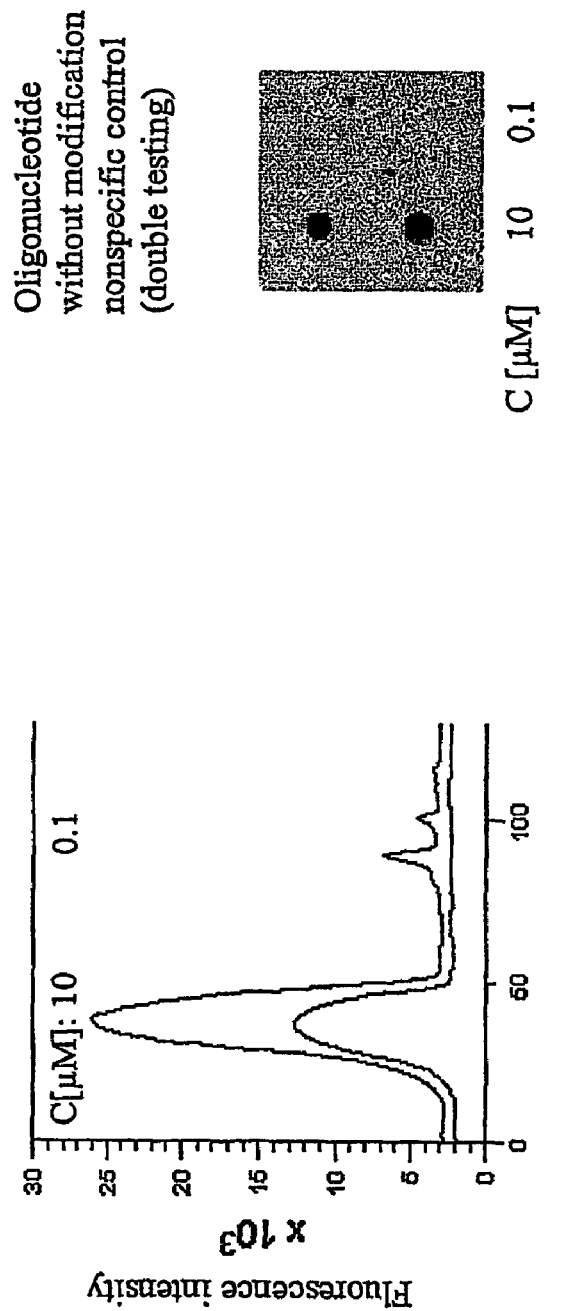
FIG. 26 displays the nonspecific attachment binding levels to the Surmodics slide used in FIG. 25.
Figure 27:
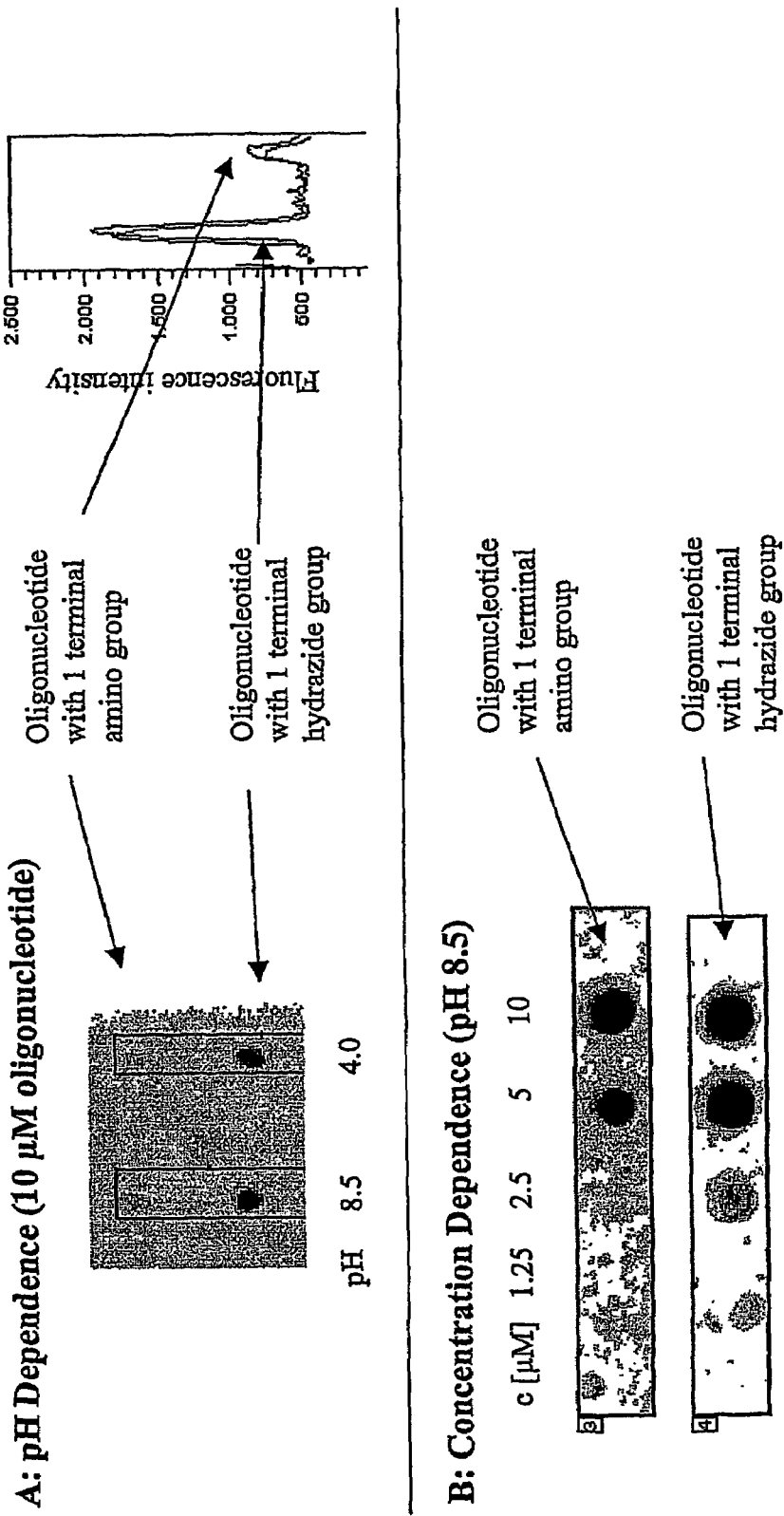
FIG. 27A shows the applicable pH range in which the hydrazide oligomers are capable of successful immobilization to a solid support.
FIG. 27B displays the improved sensitivity of a hydrazide oligomer over a standard amine modified oligomer being detectable at lower concentrations.
Figure 28:
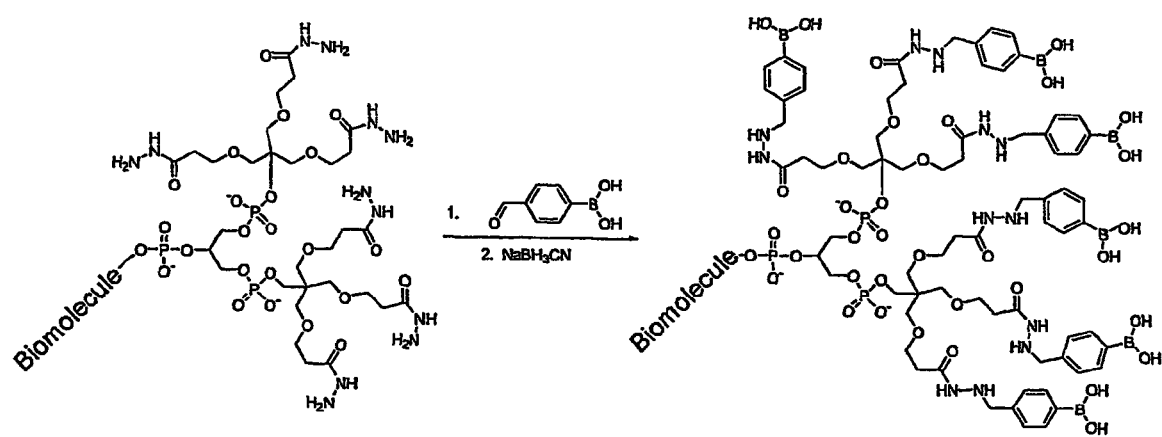
FIG. 28 illustrates one example of how a branched or unbranched hydrazide modified oligomer can be easily modified to an alternative attachment system. In this particular example a branched oligomer with six hydrazides is modified with p-formylphenylboronic acid to afford a branched PBA attachment probe.

As can be seen if FIG. 26, at both pH=8.5 and 4.0 the hydrazide oligonucleotide affords a much higher signal intensity as compared to the amine terminated oligomer and is unaffected by the change in pH. Furthermore, given the same concentrations, the hydrazide modified oligomer affords much higher signal intensity than the amine modified oligomers. The amine oligonucleotides are no longer detectable below 2.5 μM while the hydrazide oligomers are detected as low as 1.25 μM.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

p-MeNAs (methyl or methoxy phosphate nucleic acids), peptide nucleic acids (PNAs), and pyranosyl RNAs (p-RNAs).

2. The compound of claim 1, wherein Y is an oxygen.

3. The compound of claim 1, wherein Y is a sulfur.

4. The compound of claim 1, wherein —O—X—NH—NH$_2$ has the formula

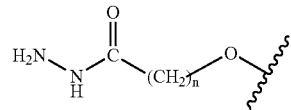

wherein n is an integer from 1–5.

We claim:

1. A compound comprising the formula:

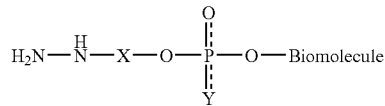

wherein X is a linear or branched, optionally substituted alkyl, aryl, or acyl group; and wherein Y is a heteroatom, and wherein the biomolecule is selected from the group consisting of a single nucleic acid, oligonucleotides, polynucleotides, DNAs, RNAs, proteins, peptides, enzymes, antibodies, CNAs (cyclohexyl nucleic acids), 5. The compound of claim 4, wherein n=5.

6. The compound of claim 1, wherein —O—X—NH—NH$_2$ has the formula

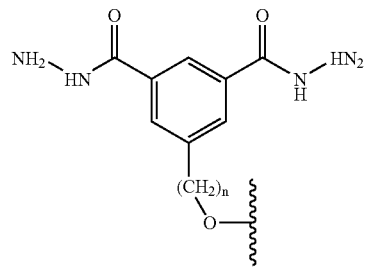

wherein n is an integer from 1–5.

7. The compound of claim 6, wherein n=1.

8. The compound of claim 1, wherein —O—X—NH—NH$_2$ has the formula

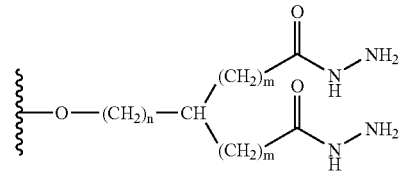

wherein n is an integer from 0–5, and wherein m is an integer from 1–5.

9. The compound of claim 1, wherein —O—X—NH—NH$_2$ has the formula

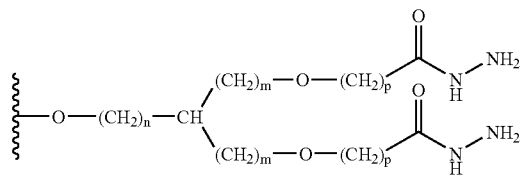

wherein n is an integer from 0–5, and wherein m and p are each independently an integer from 1–5.

10. The compound of claim 1, wherein —O—X—NH—NH$_2$ has the formula

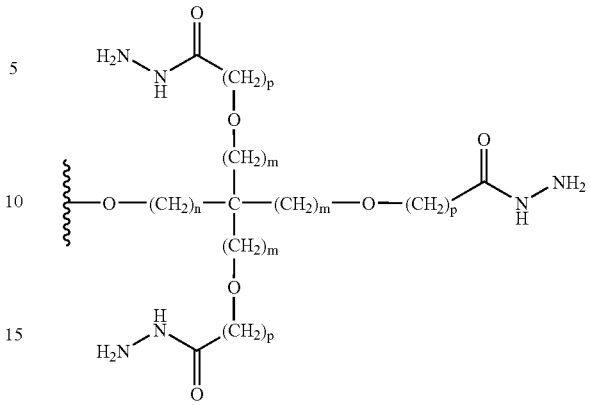

wherein n is an integer from 0–5, and wherein m and p are each independently an integer from 1–5.

11. The compound of claim 1, wherein —O—X—NH—NH$_2$ has the formula

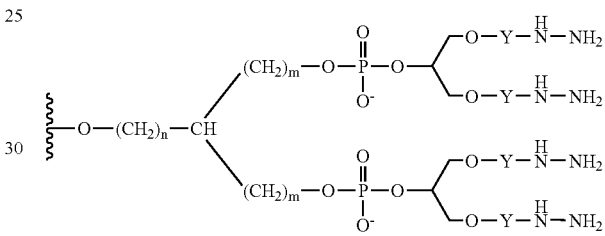

wherein n is an integer from 0–5;
wherein m is an integer from 1–5; and
wherein Y is a linear or branched, optionally substituted alkyl, aryl, or acyl group.

* * * * *

UNITED STATES PATENT AND TRADEMARK OFFICE
CERTIFICATE OF CORRECTION

| | | |
|---|---|---|
| PATENT NO. | : 7,186,813 B1 | Page 1 of 1 |
| APPLICATION NO. | : 10/181207 | |
| DATED | : March 6, 2007 | |
| INVENTOR(S) | : Schweitzer et al. | |

It is certified that error appears in the above-identified patent and that said Letters Patent is hereby corrected as shown below:

On the Title Page, please add the following:

Related U.S. Application Data and insert:

Item --(60) Provisional application No. 60/175,550, filed Jan. 11, 2000.--

Signed and Sealed this

Fifteenth Day of March, 2011

David J. Kappos
*Director of the United States Patent and Trademark Office*

SEQUENCE LISTING

<160> NUMBER OF SEQ ID NOS: 3

<210> SEQ ID NO 1
<211> LENGTH: 15
<212> TYPE: DNA
<213> ORGANISM: Homo sapien

<400> SEQUENCE: 1
tttttttttt ttttt                                                      15

<210> SEQ ID NO 2
<211> LENGTH: 19
<212> TYPE: DNA
<213> ORGANISM: Homo sapien

<400> SEQUENCE: 2
gatgagcagt tctacgtgg                                                  19

<210> SEQ ID NO 3
<211> LENGTH: 20
<212> TYPE: DNA
<213> ORGANISM: Homo sapien

<400> SEQUENCE: 3
gatgagcagt tctacgtggc                                                 20